United States Patent [19]

Hori et al.

[11] Patent Number: 5,582,576

[45] Date of Patent: Dec. 10, 1996

[54] ELECTRONIC ENDOSCOPE WITH ZOOM LENS SYSTEM

[75] Inventors: Koichiro Hori; Herbert A. Thaler, both of Framingham; Scott E. Hunt, Franklin; Philip R. Lichtman, Newton, all of Mass.

[73] Assignee: Oktas General Partnership, Westborough, Mass.

[21] Appl. No.: 319,886

[22] Filed: Oct. 7, 1994

Related U.S. Application Data

[63] Continuation-in-part of Ser. No. 967,996, Oct. 28, 1992, abandoned.

[51] Int. Cl.$^6$ ........................................... A61B 1/05
[52] U.S. Cl. ........................ 600/167; 600/118; 600/168; 600/173
[58] Field of Search ..................... 600/167, 168, 600/173, 106, 118; 359/691

[56] References Cited

U.S. PATENT DOCUMENTS

| | | | |
|---|---|---|---|
| 3,561,432 | 2/1971 | Yamaki | 600/167 |
| 3,819,267 | 6/1974 | Kawahara | 600/168 |
| 4,647,193 | 3/1987 | Rosenfeld | 356/4 |
| 4,846,155 | 7/1989 | Kimura | 600/167 |
| 4,905,668 | 3/1990 | Ohsawa | 600/167 |
| 5,191,879 | 3/1993 | Krauter | 600/167 |
| 5,214,538 | 5/1993 | Lobb | 359/691 |
| 5,222,477 | 6/1993 | Lia | 600/167 |
| 5,506,912 | 4/1996 | Nagasaki et al. | 600/103 |

*Primary Examiner*—Richard J. Apley
*Assistant Examiner*—John Leubecker
*Attorney, Agent, or Firm*—Pandiscio & Pandiscio

[57] ABSTRACT

An endoscope having an objective lens, a zoom lens, a solid state imaging device for picking up the image formed by said objective lens and transferred by said zoom lens, and control means for moving the zoom lens and the imaging device so as to assure that for each position occupied by the zoom lens the imaging device is positioned so that the its image-receiving surface is in the focal plane of the zoom lens. The endoscope also comprises first and second motion-transmitting means for moving said zoom lens and said imaging device respectively along the optical axis of said objective lens, whereby the axial spacing between said zoom lens and said objective lens and also the axial spacing between said imaging device and said objective lens may be changed, and manually operable switch means for controlling movement of the zoom lens and the imaging device by said first and second motion transmitting means. The control means also comprises means for sensing the position of said zoom lens and said imaging device along the optical axis of the endoscope, a lookup table containing data as to the spacing required to be maintained between said imaging device and said zoom lens in order for the focal plane of said zoom lens to be located substantially at the image-receiving surface of said imaging device for various positions of said zoom lens system, means for accessing said data, and means for moving said zoom lens system and/or said imaging device in accordance with the accessed data.

33 Claims, 18 Drawing Sheets

1

ELECTRONIC ENDOSCOPE WITH ZOOM LENS SYSTEM

This is a continuation-in-part of U.S. patent application Ser. No. 07/967,996, entitled "Electronic Endoscope" filed Oct. 28, 1992 by Koichio Hori, now abandoned.

BACKGROUND OF THE INVENTION

1. Field of the Invention

The present invention relates generally to endoscopes and more specifically to endoscopes which have a solid state imaging device and an optical system that includes a zoom lens unit for transmitting images to the solid state imaging device.

2. Prior Art

Endoscopes, which are instruments used to inspect cavities or openings, have found a great number of applications in medicine and other technology. In the field of medicine, the use of endoscopes permits inspection of organs or other biological specimens for the purpose of inspecting a surgical site, sampling tissue and/or facilitating the manipulation of other surgical instruments, usually with the objective of avoiding invasive and traumatizing surgical procedures.

Older conventional endoscopes used in medicine have an objective lens unit at their distal (forward) ends which transmits an image of the area forward of the objective lens unit to the proximal (rear) end of the endoscope for viewing in an eye-piece, the image being transmitted to the eye-piece via an image forwarding means in the form of a so-called relay lens set or an optical fiber bundle unit. In more recent years, in place of the eye-piece and at least part of the image forwarding means, it has been preferred to provide a small size solid state video imaging device, such as one constituting a CCD chip, in the imaging plane of the objective lens, and applying the output of that video imaging device via a suitable electronic transmission system to a video monitor for viewing by the user. With both types of image transmitting and viewing arrangements, the surgeon can view the displayed image and use the information conveyed by that image to manipulate the endoscope and also other surgical instruments that have been inserted into the patient via another incision or opening in the patient's body. In the case of endoscopes that incorporate a solid state video imaging device, the image seen by the objective lens unit can be observed in the display provided by the video monitor with or without magnification.

A critical requirement of surgical endoscopes is that the maximum cross-sectional dimension of the endoscope must be kept quite small in keeping with the objective of avoiding invasive and traumatizing surgical procedures. However, it also is necessary that the endoscope have an illumination lumen or duct of a size that will assure adequate illumination of the surgical site being inspected. In addition it is desirable to provide an optical system in the endoscope that maximizes the extent of the surgical site that is encompassed by the image seen by the surgeon (i.e., the field of view) without any substantially detrimental loss of image resolution.

In recognition of the two-fold desire to maximize the field of view and image resolution, efforts have been made by others to provide endoscopes with a zoom lens system. Such endoscopes typically include an objective lens stage, a zoom lens stage, and a focussing lens for making certain that the image passed by the zoom lens is in focus. In the case where a solid state imaging device is used in an endoscope, the desired focus control can be achieved and maintained by shifting the solid-state imaging device along the axis of the endoscope in a direction and by an amount sufficient to achieve the desired focus control.

An example of an endoscope having a zoom lens and a movable imaging device system is disclosed by U.S. Pat. No. 4,488,039, issued 11 Dec. 1984 to Masamichi Sato et al for "Imaging System Having Vari-Focal Lens For Use In Endoscope". The endoscope disclosed by Sato et al includes a control system that is adapted to estimate or calculate how much the solid state imaging device is required to be moved as a consequence of movement of the zoom lens in order to assure that the imaging surface of the imaging device is substantially at the focal plane of the zoom lens system. In essence the arrangement disclosed in U.S. Pat. No. 4,488,039 is one in which the position of the imaging device that is required to achieve proper focussing is estimated on the basis of the position of the zoom lens. However, the Sato et al endoscope is handicapped by the fact that the process of estimating or calculating an appropriate position for the imaging device in response to each new position of the zoom lens is time-consuming, due to the fact that generating the estimated positions involves continuous processing of zoom lens position data according to high order mathematical equations, with the data processing being required to provide an estimate of how much and in what direction the solid state imaging device is required to be moved to assure that the imaging surface of the imaging device is substantially in or at the focal plane of the zoom lens system. In essence the estimating is conducted "on the fly", which appears to limit the accuracy and/or response time of the system with respect to optimizing continuous focussing during movement of the zoom lens.

U.S. Pat. No. 4,488,039 also suggests that the endoscope may be modified so as to make its control system capable of detecting changes in the position of the imaging device and then estimating an appropriate position for the zoom lens in order to achieve proper focussing of the sensed image on the imaging surface of the imaging device. That arrangement also appears to suffer from the need to estimate the appropriate position for the zoom lens unit as the imaging device is being moved.

In addition to the limitations noted above, the system disclosed by U.S. Pat. No. 4,488,039 does not embody a practical electrical mechanical design that is relatively inexpensive to manufacture and also is characterized by an efficient and reliable mode of operation.

SUMMARY OF THE INVENTION

The primary object of the invention is to provide an improved electronic endoscope having a zoom capability.

Another major object of the present invention is to provide an endoscope with an imaging system which is free of the limitations of prior art electronic endoscopes having a zoom capability.

A further object of the invention is to provide a novel mechanical arrangement for providing electronic endoscope with zoom lens capability.

Another object is to provide an endoscope with an electronic imaging device that offers the advantage of incorporating a zoom lens capability without any increase in the overall cross-sectional size of the endoscope.

A further object is to provide an endoscope of the type having a zoom lens unit for varying the effective field of view and a solid state imaging device which is characterized by novel electromechanical control means for selectively changing the axial position of the zoom lens unit and/or the imaging device so as to assure that the optical image formed by the zoom lens is focussed on the image-receiving surface of the imaging device.

Still another object is to provide an improved electronic endoscope that utilizes optical fibers for illuminating the object field of the endoscope.

Another more specific object is to provide an electronic endoscope that incorporates a computer-based control system characterized by a pre-computed table of data (hereinafter called a "lookup table") containing data correlating the imaging device positions required for various zoom lens positions in order to achieve accurate focussing of the image transmitted by the zoom lens onto the image-receiving surface of the imaging device for selected object distances.

A further object is to provide an endoscope with a zoom lens and a solid state imaging device that is characterized by means for moving at least said zoom lens in accordance with operator commands, and computer-controlled means for moving said imaging device in response to movement of said zoom lens, with the degree and direction of said movement being determined by computer-stored data so as to position the image-receiving surface of said imaging device in the focal plane of said zoom lens.

In accordance with this invention, the foregoing objects are accomplished by providing an endoscope that essentially comprises an objective lens, a zoom lens, a solid state imaging device for picking up the image formed by said objective lens and transferred by said zoom, and control means for moving the zoom lens and the imaging device so as to assure that for each position occupied by the zoom lens the imaging device is positioned so that the its image-receiving surface is in the focal plane of the zoom lens. In the preferred embodiment of the invention, the endoscope comprises a tube in which the objective lens is mounted, means supporting said zoom lens and said solid state imaging device inside of said tube, first and second motion-transmitting means for moving said zoom lens and said imaging device respectively along the axis of said tube, whereby the spacing between said zoom lens and said objective lens and also the spacing between said zoom lens and said imaging device along the axis of said tube may be changed, a handle attached to said tube, and control means including manually operable switch means carried by said handle for controlling movement of said zoom lens and said imaging device by said first and second motion transmitting means, said control means being adapted to position said zoom lens and/or said imaging device so that said imaging device is substantially at the focus of said zoom lens at each position of said zoom lens. Preferably the control means comprises means for sensing the position of said zoom lens and said imaging device along the optical axis of the endoscope, a lookup table containing information as to the spacing required to be maintained between said zoom lens and said imaging device in order for the focal plane of said zoom lens to be located substantially at the image-receiving surface of said imaging device for all positions of said zoom lens system, means for accessing the data stored in said lookup table, and means for moving said zoom lens system and/or said imaging device in response to and in accordance with the accessed data.

Other objects, advantages and novel features of the invention will become more apparent from a consideration of the following detailed description when considered in conjunction with the accompanying drawings.

Figure 11:
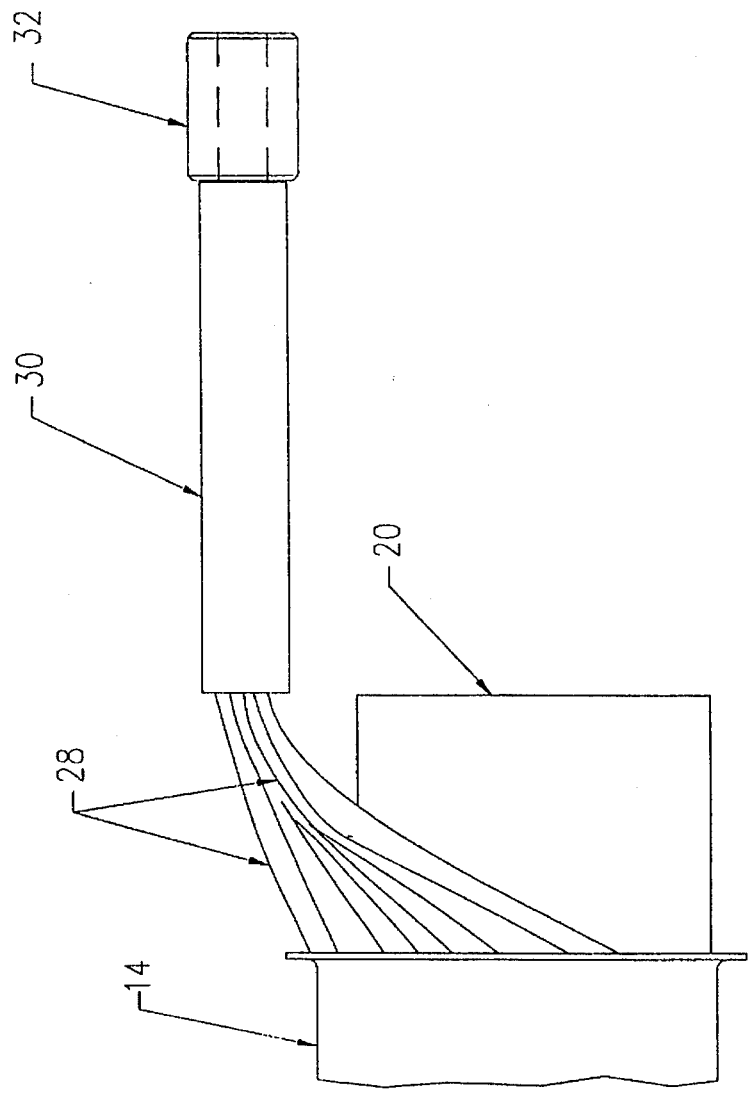
FIG. 11 is a fragmentary sectional view on an enlarged scale illustrating how the bundle of optical fibers is terminated at the proximal end of the endoscope.
Figure 11:
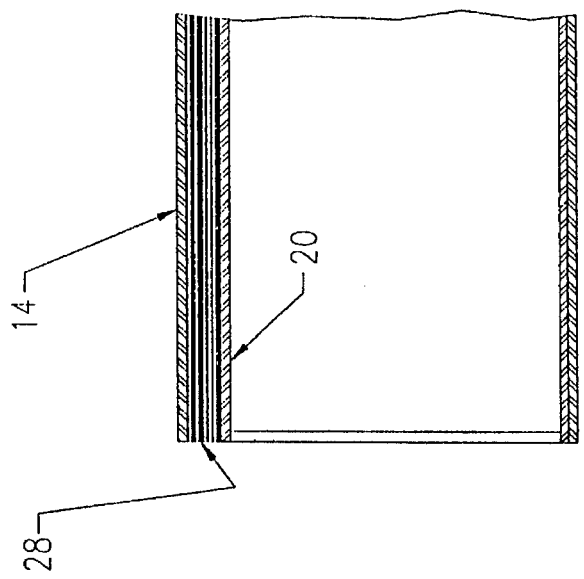

In the several views, the thickness and/or overall size of certain components are exaggerated for convenience of illustration. Thus, for example, the thicknesses of the inner and outer tubes and the diameter of the optical fibers identified hereinafter are not to scale in FIGS. 4, 9 and 11. Also, the same elements are identified by the same numerals in the several views.

DETAILED DESCRIPTION OF THE PREFERRED EMBODIMENT

Figure 1:
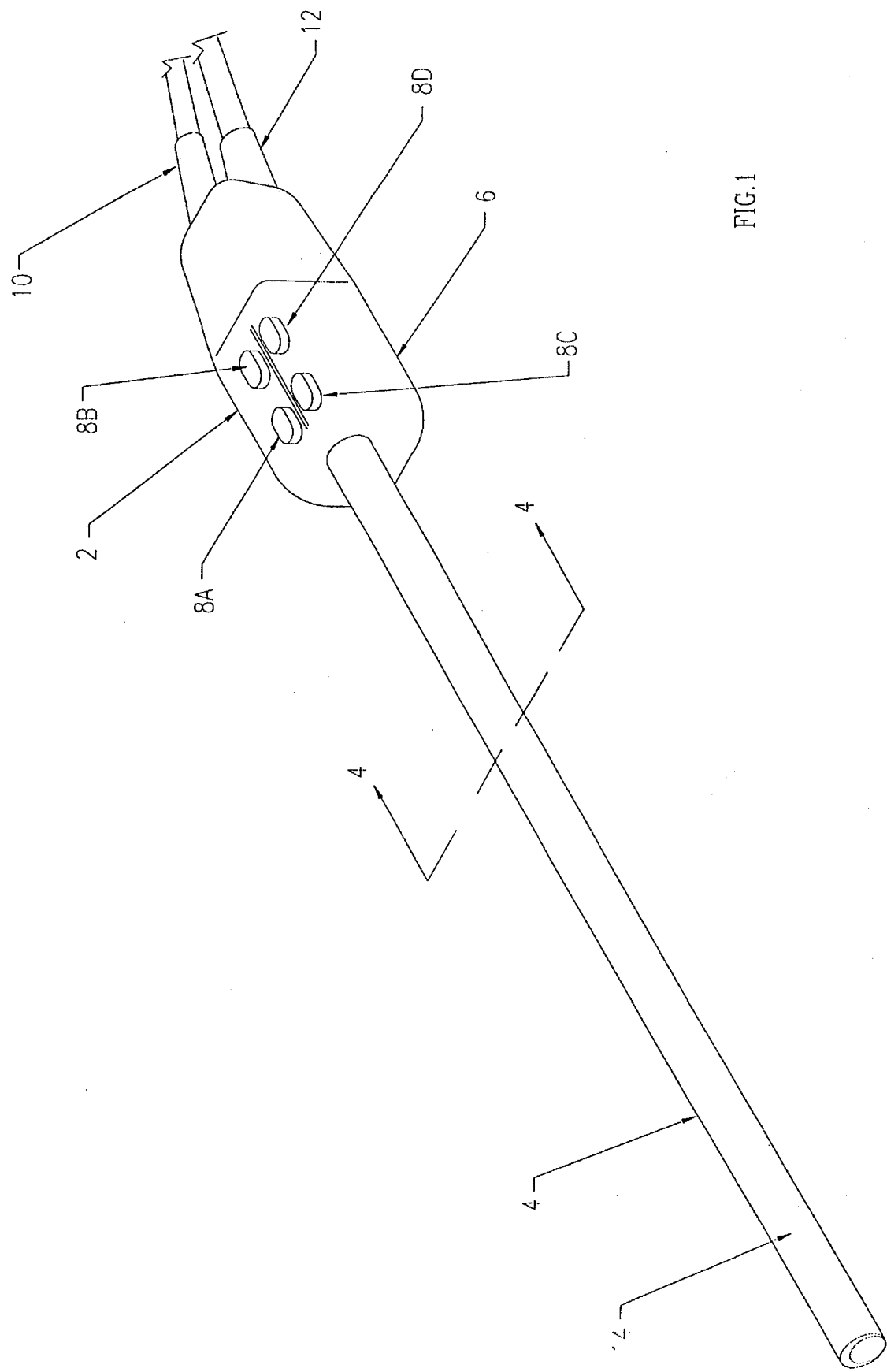
FIG. 1 is a perspective view, partially in section, illustrating a preferred embodiment of the invention.
Figure 2:
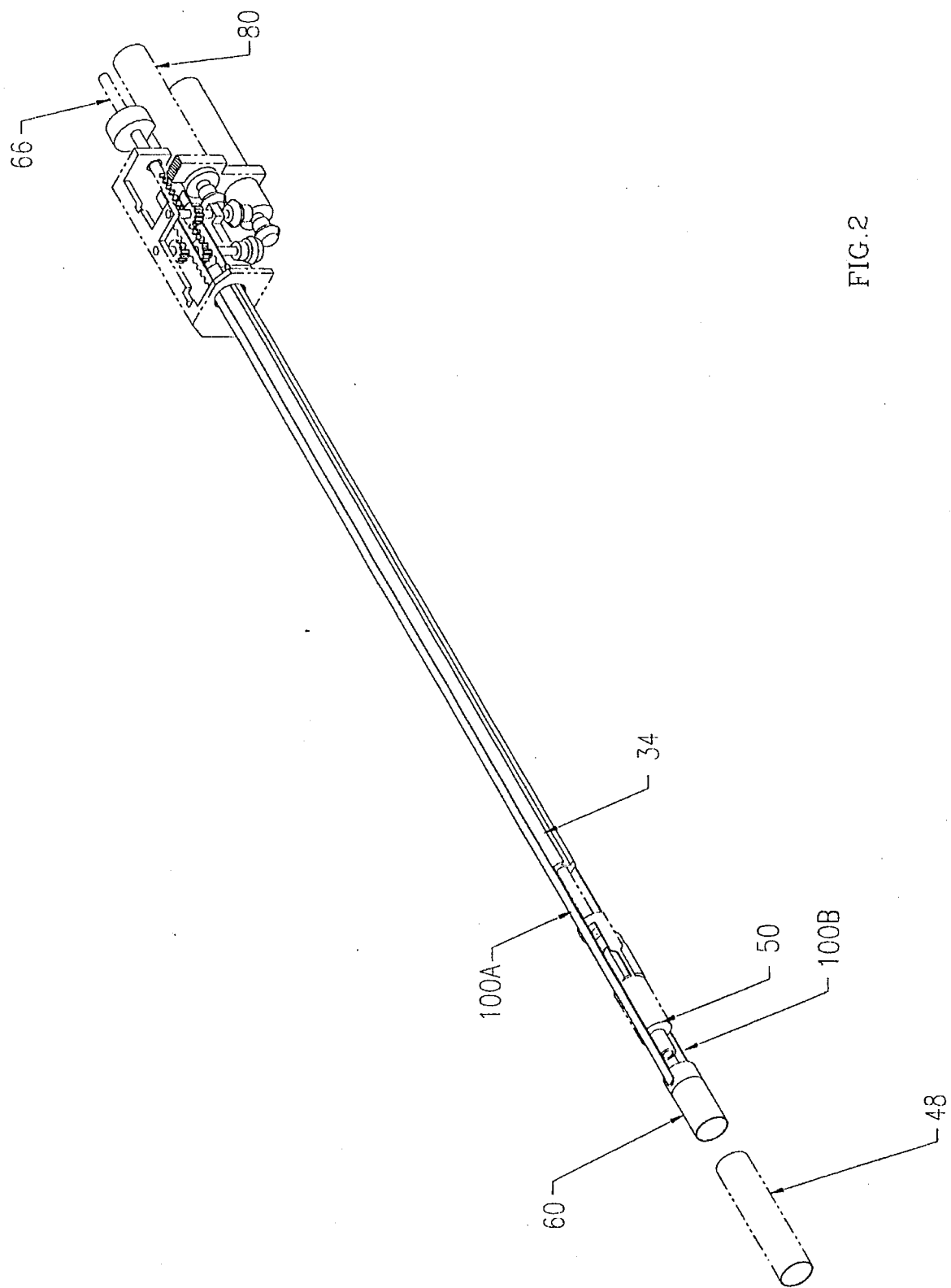
FIG. 2 is a perspective view similar to FIG. 1, with certain components removed to better illustrate the construction of the device.
Figure 8:
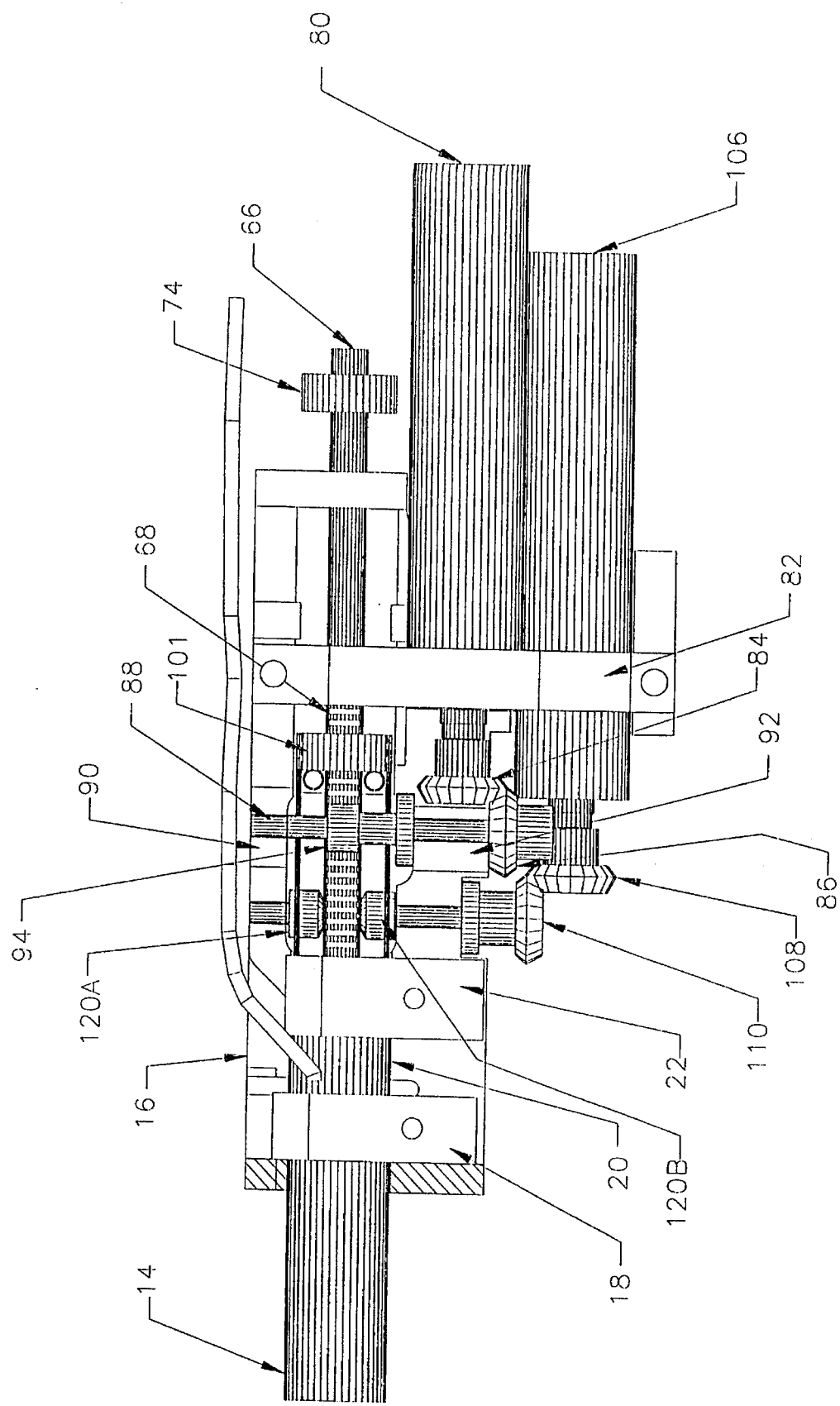
FIG. 8 is a side view in elevation further illustrating the drive trains for the zoom lens unit and the imaging device.

Referring first to FIG. 1, there is illustrated an electronic endoscope comprising a handle unit 2 and an elongate tubular assembly 4. Handle unit 2 comprises a housing 6 with openings through which four control switch buttons 8A–8D protrude. A fiber optic cable 10 and an electrical cable 12 are attached to the proximal (rear) end of housing 6. The elongate tubular assembly 4 comprises a cylindrical outer tube 14 which is open at its distal (front) end. The proximal end of tube 14 extends into housing 6 and is secured by a clamp 18 to a first portion of a mounting frame 16 (FIGS. 2 and 8). Housing 6 preferably consists of two or more mating parts that are releasably secured to one another and frame 16 by suitable screw fasteners (not shown). Mounted within outer tube 14 is a cylindrical inner tube 20

(FIGS. 4, 5 and 8) which has its distal (front) end terminating substantially in the same plane as the corresponding end of the outer tube. The proximal end of inner tube 20 extends beyond the corresponding end of outer tube 14 and is anchored by a clamp 22 (FIG. 8) to a second portion of frame 16.

Figure 4:
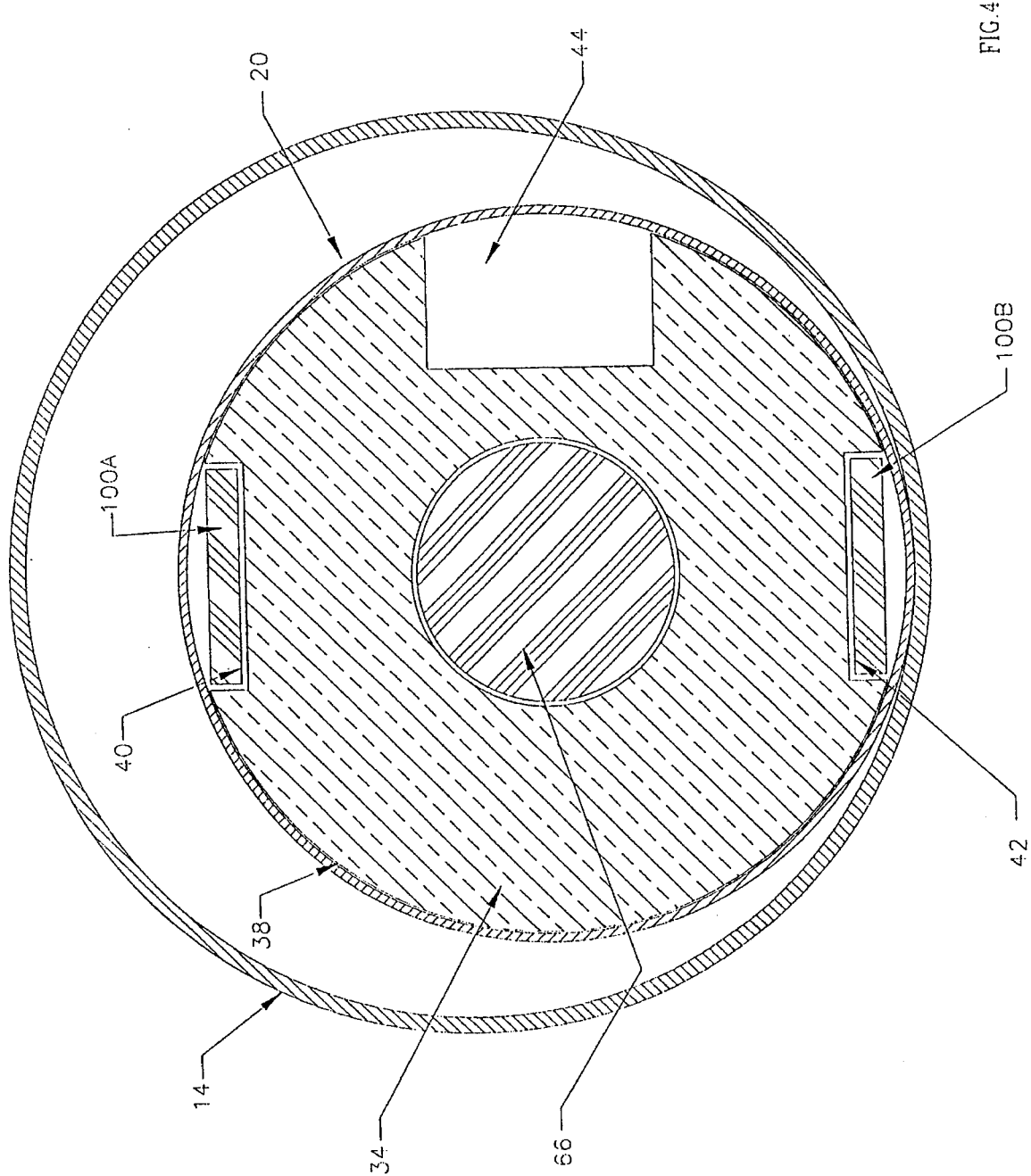
FIG. 4 is a cross-sectional view on a greatly enlarged scale taken along line 4—4 of FIG. 1.
Figure 9:
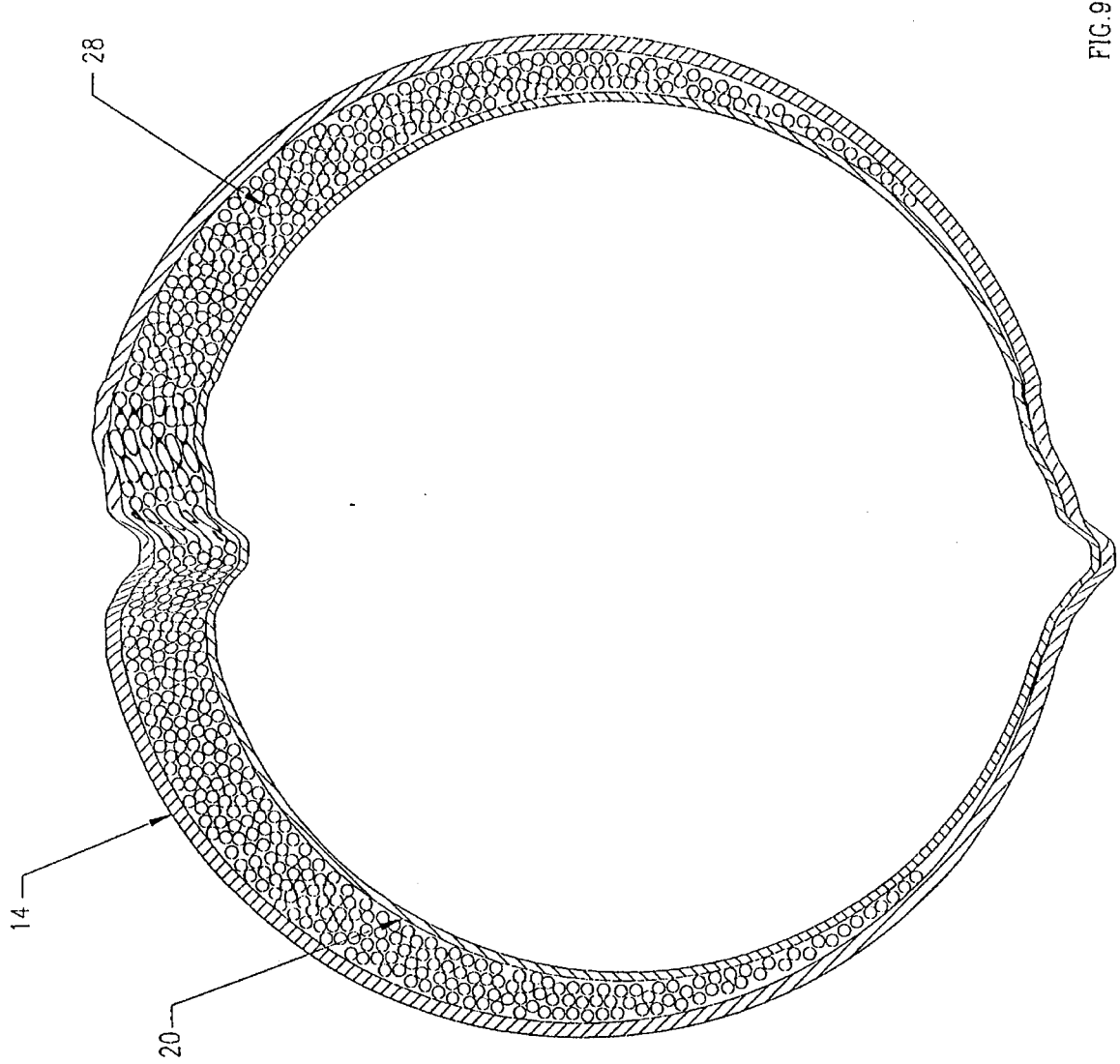
FIG. 9 is a front end view of the endoscope illustrating the disposition of the optical fibers used to illuminate the surgical site.

As seen in FIGS. 4 and 9 the inner tube is smaller than and is mounted eccentrically to the outer tube, so as to leave a crescent shaped area to accommodate a plurality of optical fibers 28 (FIGS. 9 and 11) that are used to transmit light to illuminate the surgical site, i.e., the objective lens field of view. The distal (forward) ends of fibers 28 may (but need not) be bonded to one another by a suitable cement such as an epoxy resin; in either case, the fibers are locked in place between the two tubes, with their forward ends being optically polished and terminating substantially flush with the plane of the distal end edge of the outer tube. Fibers 28 project out of the rear end of outer tube 14 and are collected in a protective tubing 30 preferably made of a material such as a silicone rubber. The rear ends of fibers are captured in a ferrule 32 that is used to connect it to cable 10. The rear end surfaces of fibers 28 are optically polished.

Figure 5:
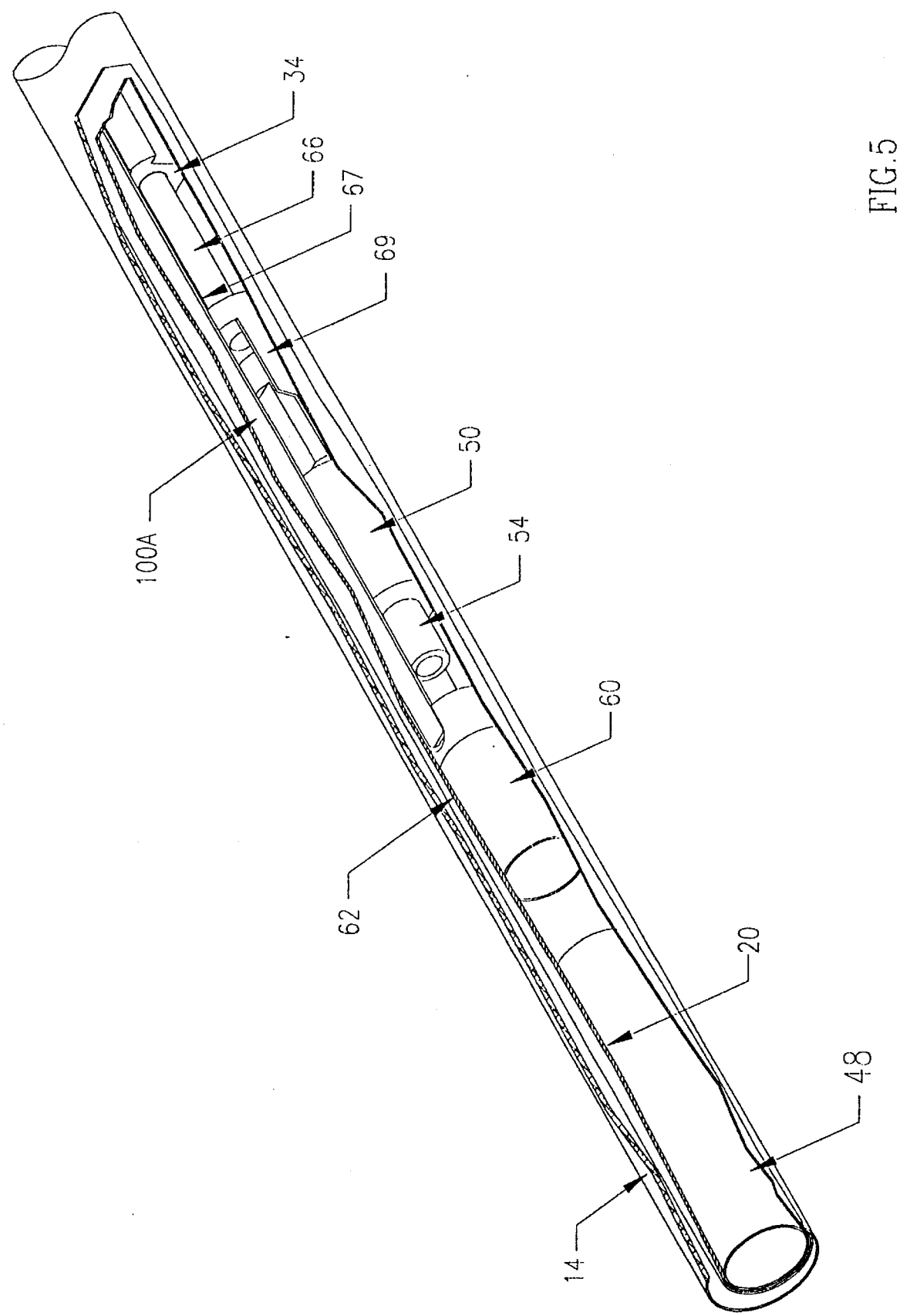
FIG. 5 is a perspective view on an enlarged scale of certain components of the endoscope, with certain components broken away.
Figure 10:
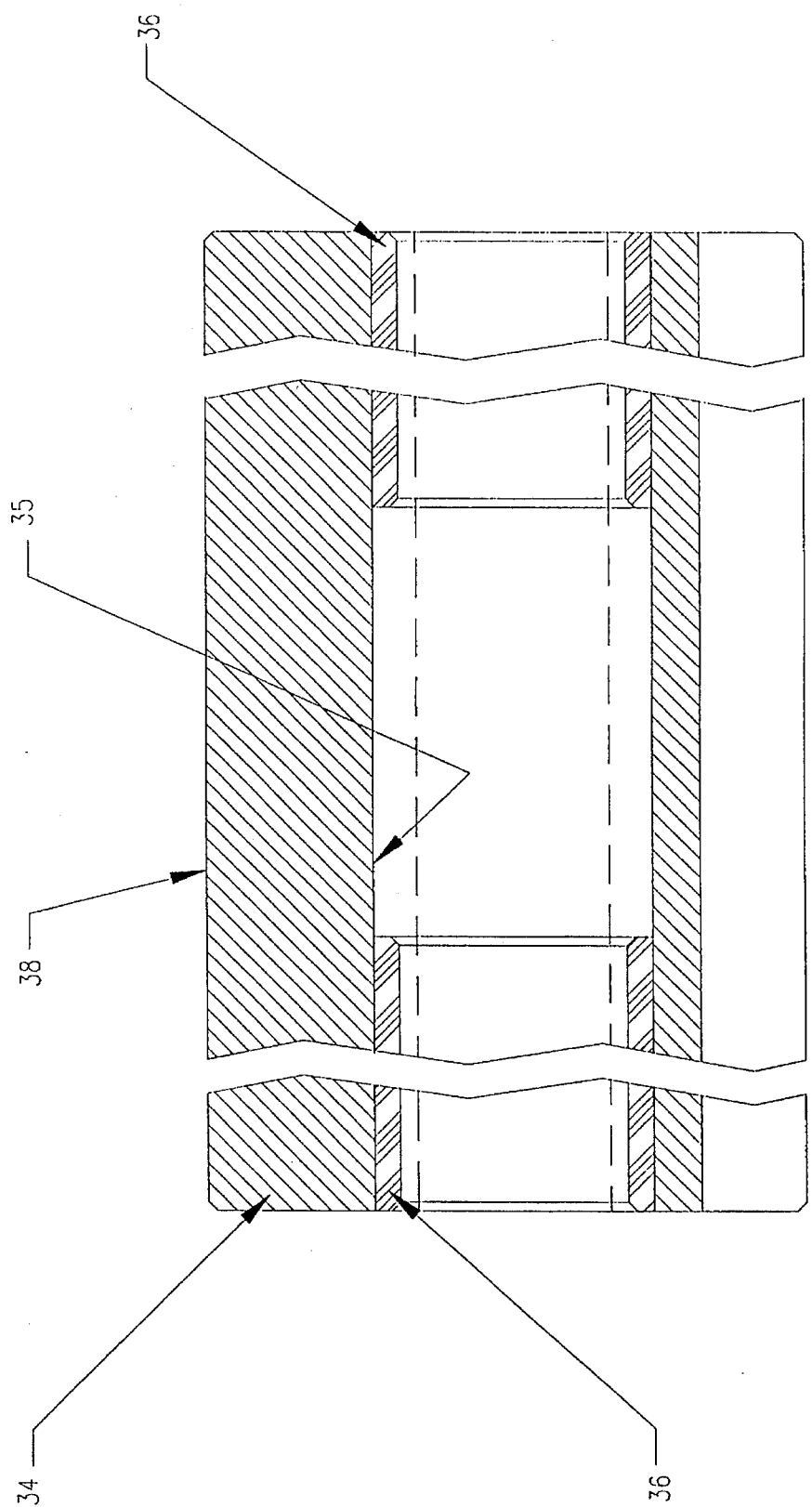
FIG. 10 is a fragmentary sectional view in elevation of the elongate bushing used to support the drive rod for the imaging device.

Referring now to FIGS. 2, 4, 5 and 10, mounted within and locked to inner tube 20 is an elongate bushing 34 that has a sleeve bearing 36 located at each end of its central bore or lumen 35 (FIG. 10). Bearings 36 are made of a material having a low coefficient of friction. The proximal (rear) end of bushing 34 terminates substantially flush with the corresponding end of inner tube 20. The forward end of bushing 34 terminates intermediate the opposite ends of tube 20 (FIG. 5). As seen in FIG. 4, bushing 34 has a generally cylindrical outer surface 38 sized so that it makes a close or tight fit with the inner surface of inner tube 20. The generally cylindrical outer surface of the bushing is disrupted by three axially extending grooves 40, 42 and 44. Grooves 40 and 42 are identical in shape and are diametrically opposed to one another, while groove 44 is somewhat deeper. The purpose of grooves 40, 42 and 44 is described hereinafter.

As seen in FIGS. 1, 2, 3, 5 and 6, mounted within the front end of and fixed to inner tube 20 is an objective lens unit 48. Details of the objective lens unit are not provided since such units are well known to persons skilled in the art. See, for example, U.S. Pat. Nos. 4,488,039; 4,491,865; 4,745,470; 4,745,471; 4,832,003; 4,867,137; and 5,122,650. However, it is to be appreciated that the objective lens unit may consist of one or more lenses. Inner tube 20 may be fitted with a separate transparent window member (not shown) disposed at its front end in front of the objective lens unit, or the front element of the objective lens unit may serve as the window.

Figure 6:
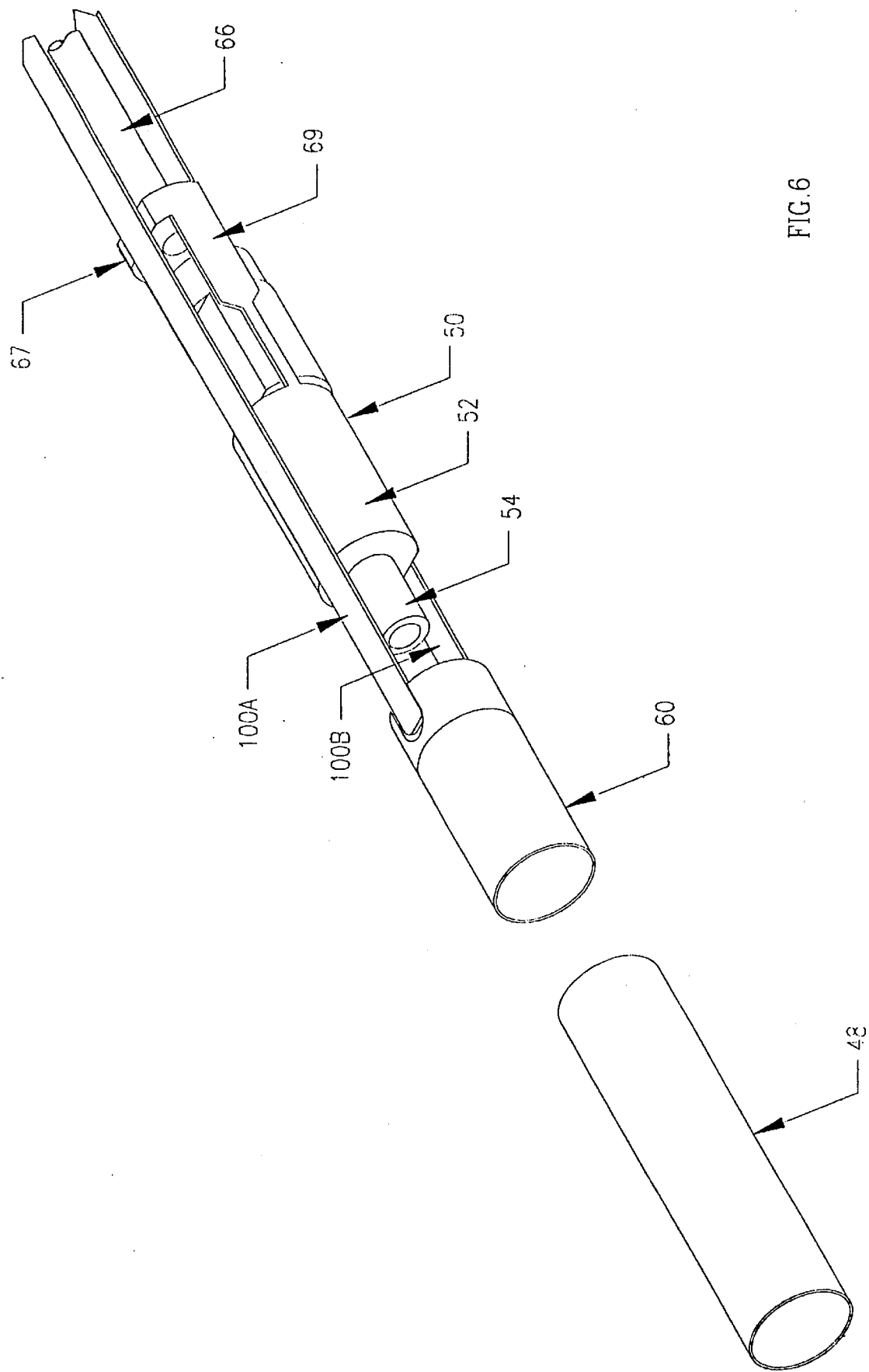
FIG. 6 is a fragmentary exploded view on an enlarged scale of certain components of the endoscope.

Also disposed within inner tube 20 is a cylindrical video imaging unit 50 (FIGS. 2, 3, 5, 6). Exact details of imaging device 50 are not illustrated since its form is not critical to the invention and instead it may take various forms, e.g., it may be like the ones described and illustrated in U.S. Pat. Nos. 4,448,039; 4,491,865; 4,867,137; and 5,166,787. Unit 50 comprises a solid state CCD semi-conductor imaging device (not shown), preferably one comprising a CCD chip as shown in U.S. Pat. Nos. 4,745,470; 4,745,471; and 5,021,888, mounted within a cylindrical housing 52 that is sized to make a close sliding fit in inner tube 20. As seen in FIGS. 5 and 6, the forward end of housing 52 is provided with a cylindrical tubular extension 54 that serves as an aperture for the solid state imaging device. Also, although not shown, it is to be understood that the solid state CCD device has a lead frame or chip carrier with terminal pins adapted to mate with a conventional connector (not shown) on the end of a multi-strand wire cable (also not shown) that extends rearwardly in groove 44 of bushing 34 and is coupled to electrical cable 12, whereby the imaging device is coupled to external electronic circuits as hereinafter described.

Also mounted within inner tube 20 is a zoom lens unit 60 (FIGS. 2, 3, 5 and 6). Details of the zoom lens unit are not provided since its exact form is not critical to the invention and also since such units are well known to persons skilled in the art of optics (see, for example, U.S. Pat. Nos. 4,570,185 and 4,781,448). Zoom lens unit 60 may comprise one or more lenses, according to the desired zoom range and image resolution. In the preferred embodiment of the invention, the lens or lenses of zoom lens unit 60 are contained within a cylindrical housing 62 that is sized to make a close sliding fit in inner tube 20.

Separate means are provided for moving imaging device 50 and zoom lens unit 60, such means taking the form of electrically powered drive means and motion transmitting means as shown in FIGS. 2–8.

The motion transmitting means for imaging device 50 comprises a cylindrical drive rod 66 that extends through bushing 34 and makes a close sliding fit with its two end sleeve bearings 36. Rod 66 has a length sufficient for its opposite ends to project from the corresponding forward and rear ends of bushing 34 when the rod is in both its distal (forward) and proximal (rear) limit positions which are described hereinafter. Video imaging unit 50 is attached to the distal (front) end of rod 66 by a cylindrical coupling member 67 (FIGS. 3, 5, 6) that is sized to make a close sliding fit in inner tube 20. Coupling member 67 has a pair of forwardly extending, diametrically opposed arms 69 (only one of which is visible in FIGS. 5 and 6) that have their forward ends connected to the imaging unit, whereby the imaging unit will move with rod 66 when the latter is moved axially relative to inner tube 20.

Figure 3:
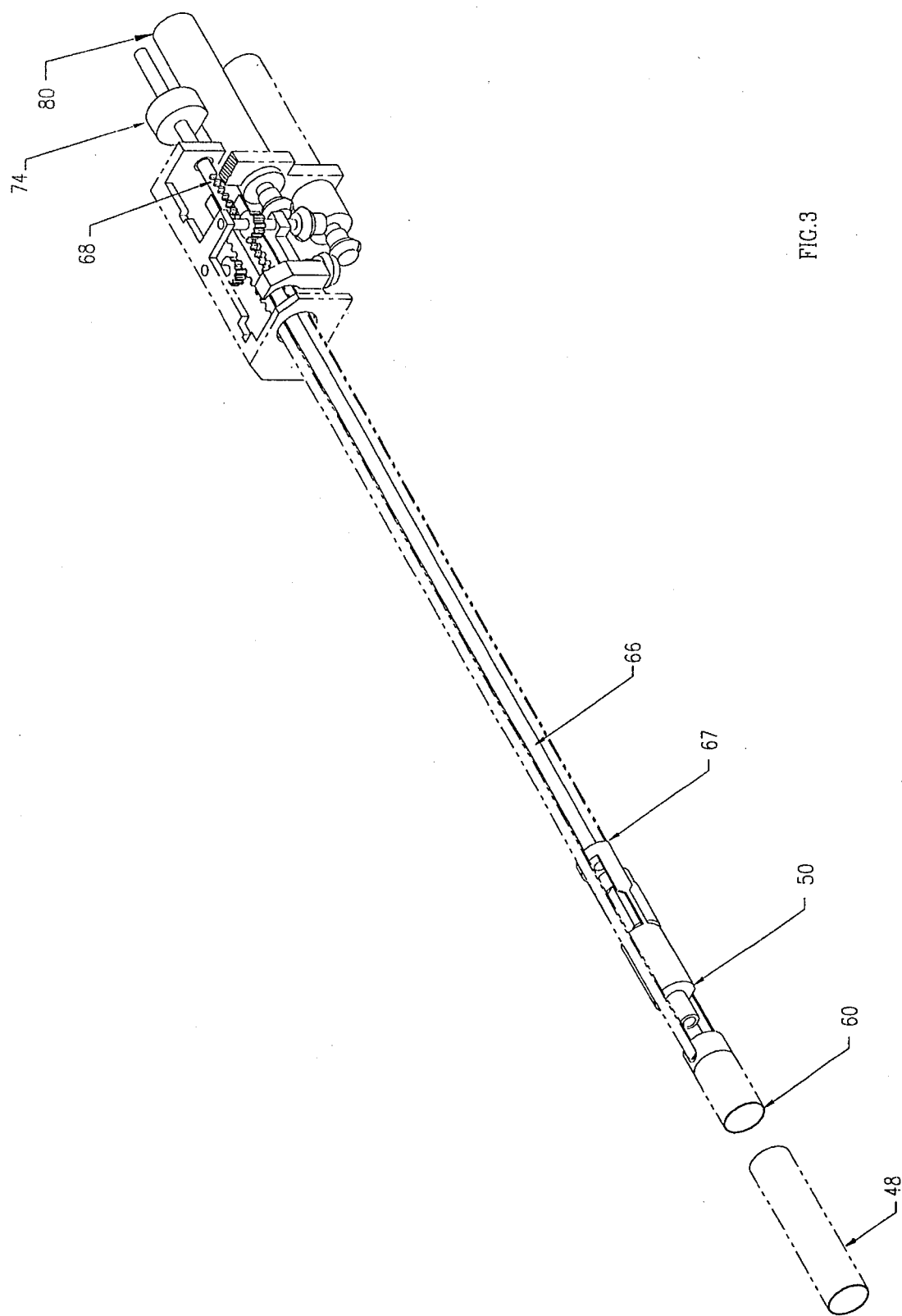
FIG. 3 is a view similar to FIG. 2, but with additional components removed to better illustrate the construction.
Figure 7:
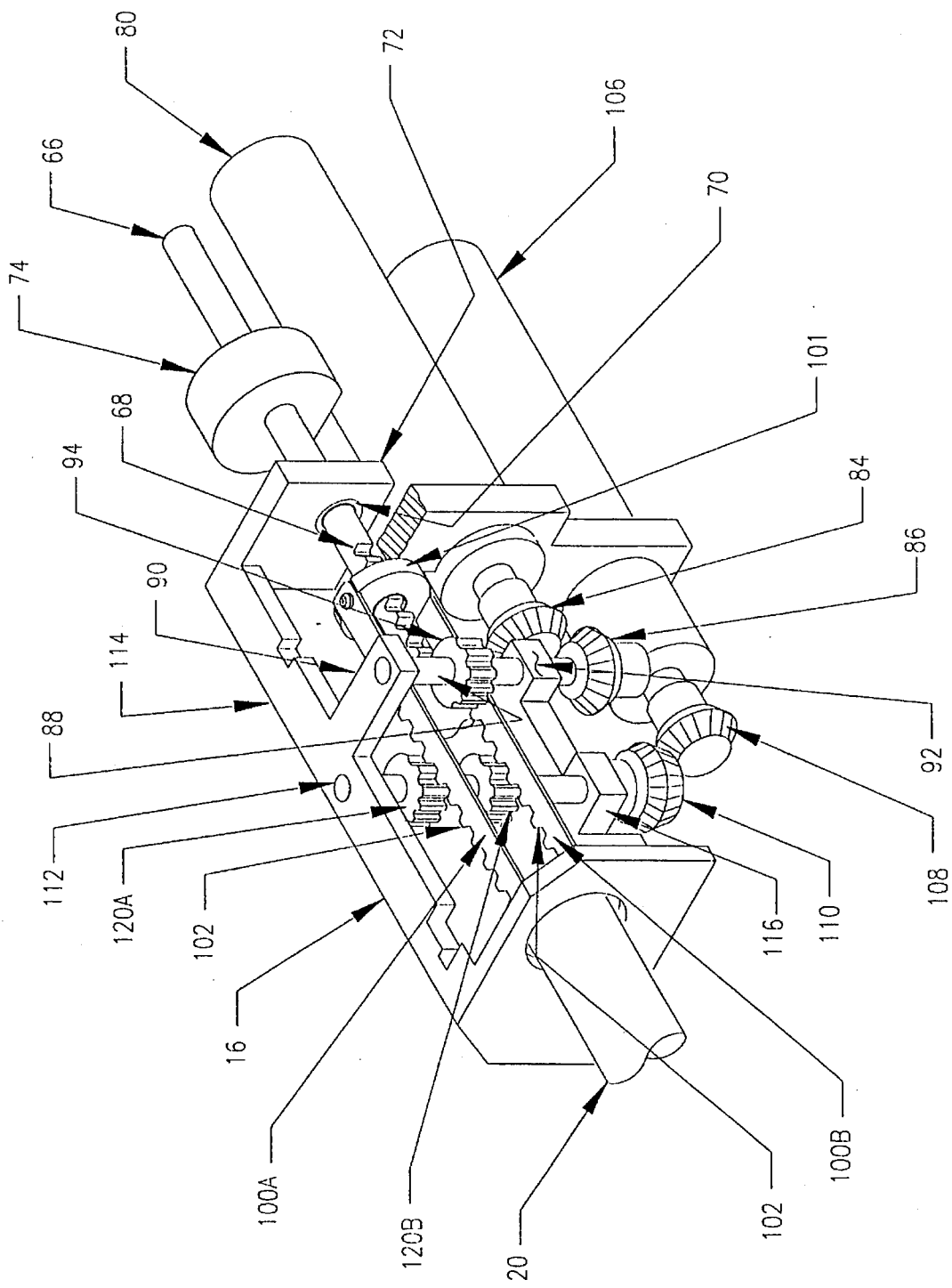
FIG. 7 is an enlarged fragmentary perspective view illustrating the drive trains for the zoom lens unit and the imaging device, with portions broken away.

As seen in FIGS. 3, 7 and 8, the proximal (rear) end of rod 66 is provided with a series of evenly spaced gear teeth 68, which permit rod 66 to function as a first gear rack. Gear teeth 68 extend over a relatively short length of rod 66 and terminate short of the proximal (rear) end of the rod. The portion of rod 66 that protrudes from the rear end of bushing 34 extends through and is slidably mounted by a bushing 70 that is mounted in a portion 72 of frame 16. Mounted on rod 66 between its proximate end and teeth 68 is a stop member 74 which is positioned to be intercepted by portion 72 of frame 16 when the rod is moved forward. Stop member 74 and frame portion 72 coact to determine a first (forward) limit position for rod 66 and imaging device 50. A second (rear) limit position for rod 66 and imaging device 50 is determined by engagement of the proximal (rear) end of imaging device housing 52 with the forward end surface of bushing 34.

The drive means for imaging device 50 comprises a reversible electrical d.c. motor 80 attached to frame 16. Motor 80 is identified hereinafter as the "focus motor" since in the invention's automatic mode of operation its function is to move imaging unit 50 so that the image-receiving surface of its CCD component is located in the focal plane of zoom lens unit 60. The output shaft of motor 80 carries a pinion gear 84 that forms part of a gear system for drive rod 66. Gear 84 meshes with a second pinion gear 86 affixed to a shaft 88 that is rotatably supported by portions 90 and 92 (FIG. 7) of frame 16. Shaft 88 in turn carries a gear 94 (FIG. 7) that meshes with teeth 68 on rod 66, whereby rotation of shaft 88 by operation of motor 80 will cause linear motion of shaft 66 and imaging device 50 in a direction determined by the direction of movement of the output shaft of that motor.

As seen in FIGS. 2 and 4–8, the motion transmitting means for zoom lens unit 60 comprises two elongate flat rods 100A and 100B that are sized to snugly and slidably fit in grooves 40 and 42 of bushing 34. Grooves 40 and 42 have a depth that assures that rods 100A and 100B will not protrude beyond the periphery of bushing 34. The front (distal) ends of rods 100A,B are connected to housing 62 of the zoom lens unit. It is to be noted that coupling member 67 has two diametrically opposed grooves 71 (only one is shown in FIG. 6) to slidably accommodate rods 100A and 100B within tube 20. Grooves 71 are sized so as to make a close sliding fit with rods 100A,B and also so that rods 100A and 100B will not protrude beyond the periphery of coupling member 67. The rear ends of rods 100A, 100B are attached to a collar 101 that surrounds and makes a close sliding fit with rod 66. The proximal (rear) ends of rods 100A,B also are provided with a series of evenly spaced gear teeth 102 (FIG. 7).

The drive means for zoom unit 60 comprises a reversible electrical d.c. motor 106. Both it and motor 80 are attached to frame 16 by a removable clamp 82. Motor 106 is identified hereinafter as the "zoom motor". The output shaft of motor 106 carries a pinion gear 108 that meshes with a pinion gear 110 that is mounted on and secured to a shaft 112. The latter is rotatably mounted to mutually spaced portions 114, 116 of frame 16. Shaft 112 carries two axially spaced gears 120A and 120B that mesh with teeth 102 on rods 100A and 100B respectively, whereby rotation of shaft 112 by operation of motor 106 will cause linear motion of rods 100A and 100B, and thereby zoom lens unit 60, lengthwise of inner tube 20 in a direction determined by the direction of rotation of the output shaft of the motor. Axial movement of zoom lens unit 60 is limited by two separate stop means. The forward limit position is determined by engagement of collar 101 with two stop pins 103 affixed to frame 16. The rear limit position is determined by engagement of collar 101 with frame portion 72. The two mechanically-determined limit positions are set so as to permit the zoom lens unit a suitable total travel distance therebetween.

Figure 13:
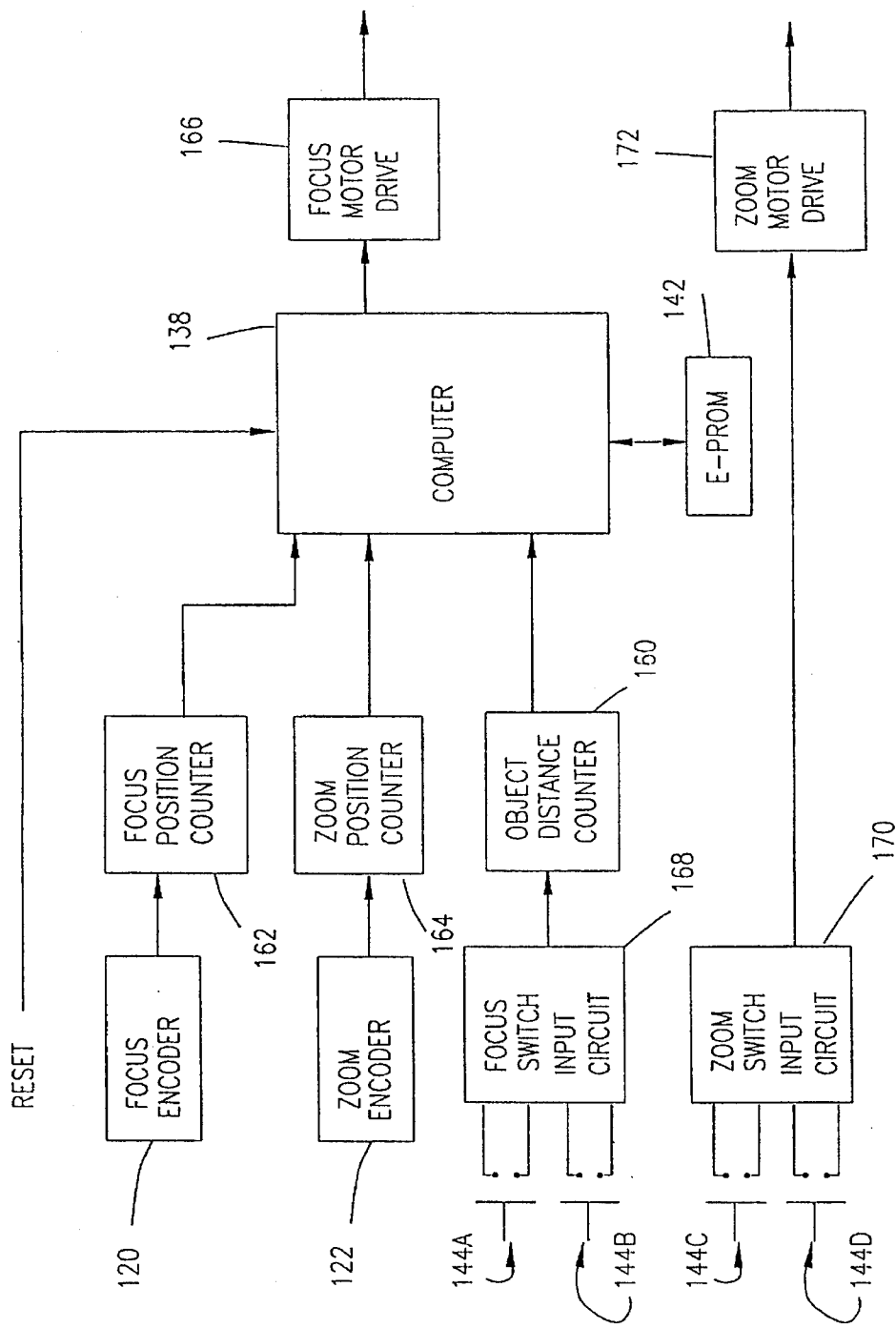
FIG. 13 is a block diagram identifying components of the control system for the endoscope, including certain components established by programming of the computer that form part of the control console.

Referring now to FIG. 13, the housings of focus motor 80 and zoom motor 106 include position-sensing encoders represented schematically at 120 and 122 that are coupled to the output shafts of the motors and are designed to provide pulse-type signal outputs that are polarized plus or minus according to the direction of movement of the output shafts of motors 80 and 106 respectively. Shaft encoders 120 and 122 may take various forms but preferably they are incremental digital encoders. Because incremental position-sensing shaft-coupled encoders are well known, details of construction of the encoders are not provided herein.

Figure 12:
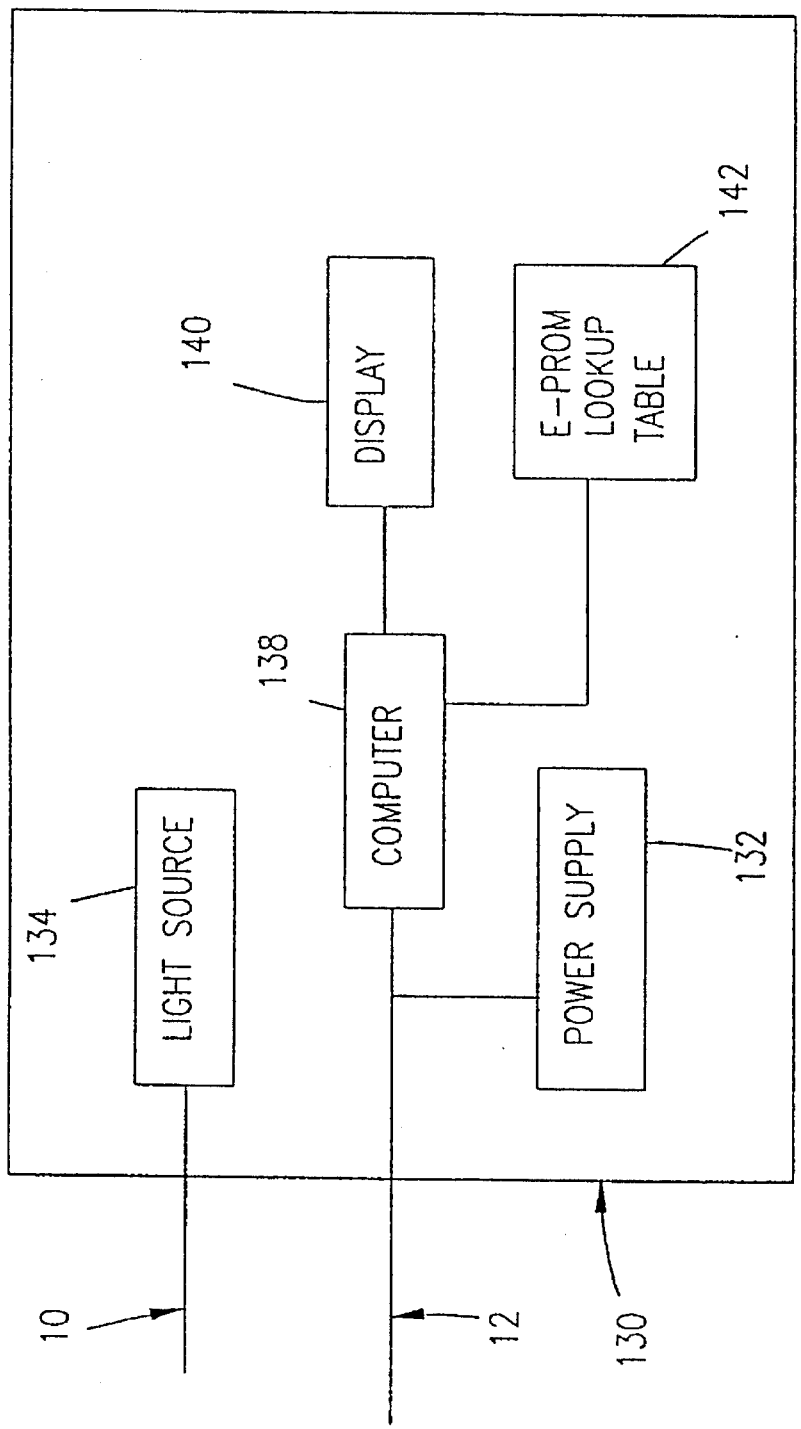
FIG. 12 is a schematic view of the electronic control console to which the endoscope of FIG. 1 is connected.

FIG. 12 diagrammatically illustrates an electronic console 130 to which the endoscope is coupled. Essentially the console comprises a light source 134 for the endoscope, an electronic controller comprising a digital computer 138 (which includes a microprocessor and associated memory, control and input and output circuits), a display module 140 that includes a CRT display device (not shown) whereby the surgeon or other user may monitor the images seen by the endoscope, an electronic memory device 142, preferably but not necessarily in the form of an E-prom, that serves as a zoom/focus lookup table as hereinafter described, and a power supply 132 for the solid state imaging unit 50, motors 80 and 106, and the electronic controller. Power supply 132, light source 134, computer 138, display module 140 and E-prom 142 are interconnected as represented schematically in FIG. 12 so as to permit the mode of operation described hereinafter. Although not shown, it is to be understood that power supply 132 includes a manually operated main power switch (not shown) which is used to turn the instrument "on" and "off".

Optical fiber cable 10 is coupled to console 130 so as to be able to transmit light from light source 134 to light fibers 28, whereby when that light source is energized by operation of the controller, the resulting light beam will illuminate the objective field of view. Multi-wire cable 12 is connected at its outer end to power supply 132 and computer 138; at its inner end cable 12 has certain of its wires coupled by a connector (not shown) to terminals of the CCD chip of imaging device 50 and others of its wires connected to motors 80 and 106 and the control switches associated with buttons 8A–8D.

Referring again to FIG. 13, the switch buttons 8A and 8B form part of two focus control switches 144A and 144B, while switch buttons 8C and 8D form part of two zoom control switches 144C and 144D. Preferably, a second like set of foot-operated switches (not shown), are added in parallel with switches 144A–D so as to give the surgeon the option of controlling maneuvering of imaging device 50 and zoom lens unit 60 using one of his feet rather than one of his hands. As explained further hereinafter, operating switch 144A will energize focus motor 80 so as to cause the imaging device to move forward toward the distal end of inner tube 20, while operating switch button 144B will energize focus motor 80 so as to cause reverse movement of the imaging device. Similarly, operating switch button 144C will energize motor 106 so as to cause the zoom lens unit to move forward toward the distal end of inner tube 20, while operating switch 144D will energize motor 106 so as to cause reverse movement of the zoom lens unit. Moving the zoom lens unit forward causes the field of view seen by the imaging device to narrow while moving the zoom lens unit rearward causes the field of view to widen. It is preferred that the zoom lens unit be designed to "zoom" between a field of view of about 20 degrees to one of about 70 degrees.

Computer 138 is configured by its software program to provide an object distance counter 160, a focus/CCD position counter 162, and a zoom position counter 164. The computer is arranged to provide a control signal to a focus motor drive circuit 166 that preferably forms part of the controller 130. Switches 144A and 144B are connected to a focus switch input circuit represented schematically at 168 that provides an input to object distance counter 160, while switches 144C and 144D are connected to a zoom switch input circuit 170 that provides control signals to a zoom motor drive circuit 172.

Figure 14:
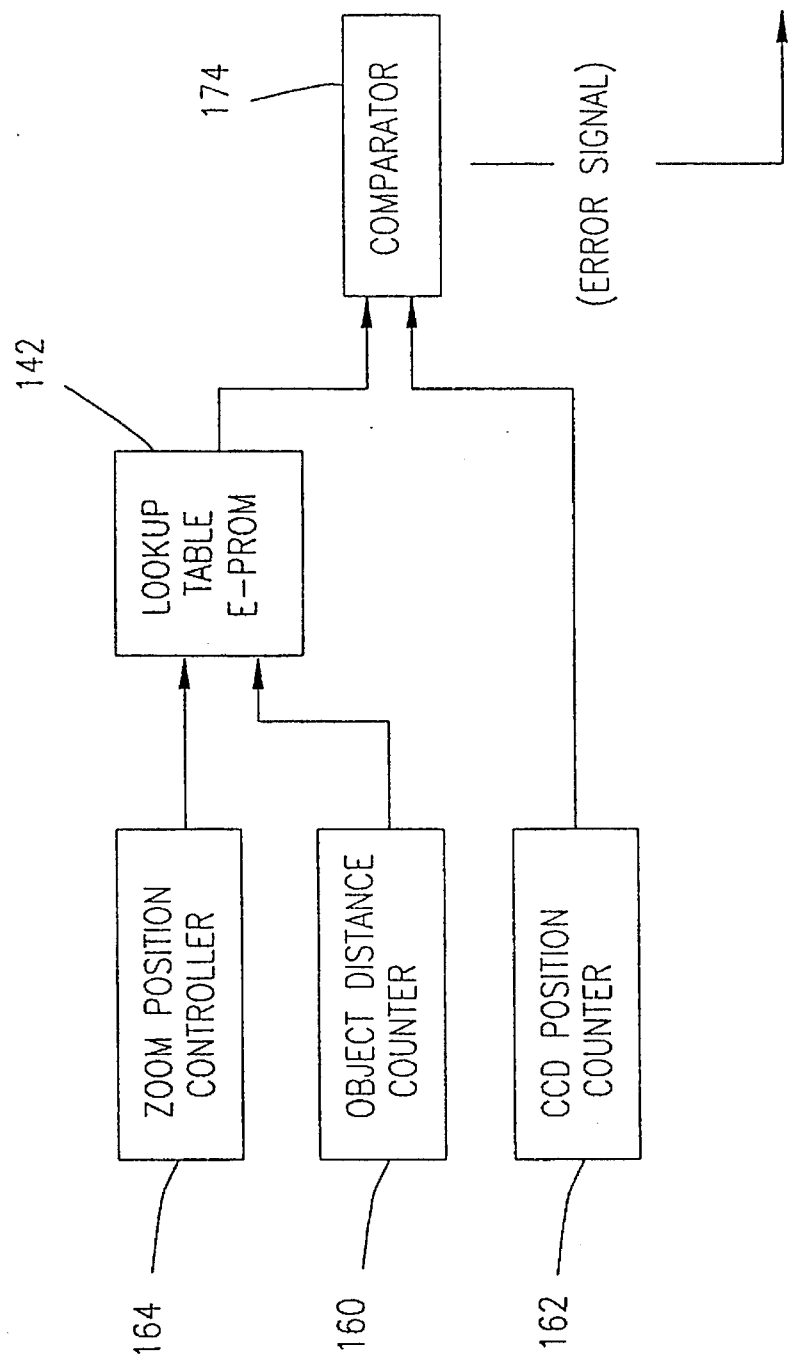
FIG. 14 is a schematic view further illustrating the control system.

Counters 162 and 164 provide outputs that permit computer 138 to determine the extent of rotation of the output shafts of motors 80 and 106 from pre-selected positions which are stored in E-prom 142, whereby at any given time the counts in the counters represent the exact positions of imaging device 50 and zoom lens unit 60 (in relation to the pre-selected reference positions along the axis of tube 20). As illustrated in FIG. 14, the computer is configured so that (1) the outputs from object distance counter 160 and zoom position counter 164 are applied to E-prom 142 to obtain a position data output signal according to those counter outputs and (2) the output signal obtained from E-prom 142 and the output of focus/CCD position counter 162 are applied to a comparator or adder 174 (established by computer programming), with the output of the comparator being an error signal that is supplied to focus motor drive 166.

Figure 15:
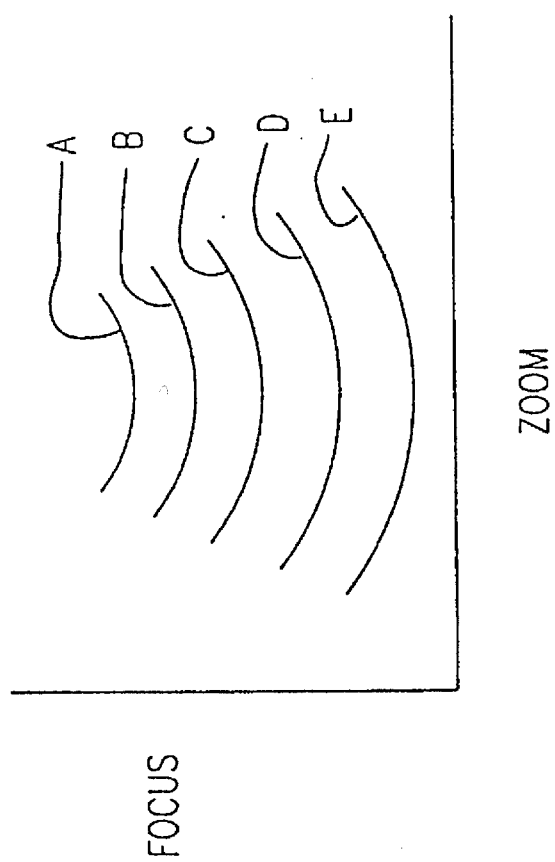
FIG. 15 illustrates the type of curves that are recorded in a lookup table that forms part of the invention.
Figure 16:
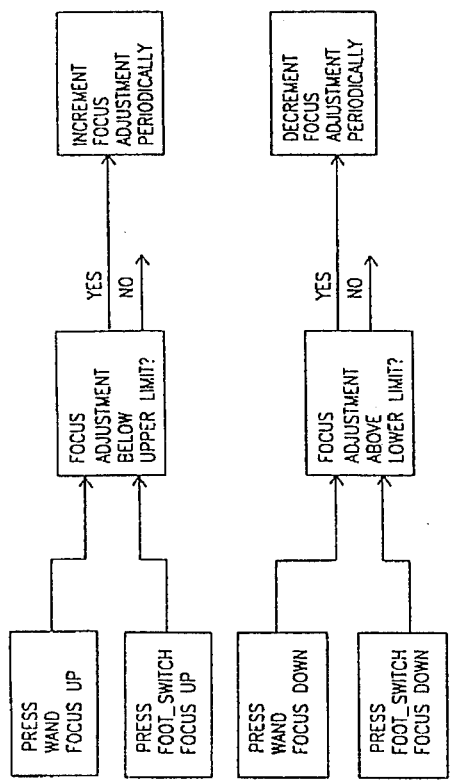
FIGS. 16–19 are flow diagrams illustrating the mode of operation established by the computer software program embodied and/or used with the controller of the endoscope.

FIG. 15 relates to the kind of data that constitutes the zoom/focus lookup in table E-prom 142. In FIG. 15, each of the curves A–E is a plot of different positions of (1) the zoom lens in relation to the objective lens ("Zoom") versus (2) the corresponding distances between the CCD imaging device and the objective lens unit ("Focus") that is required to assure that the image-receiving surface of the imaging device is in the focal plane of the zoom lens unit. Each of the curves A–E is for different object distances. As used herein, the term "object distance" means the distance measured from the objective lens to the viewed object. By way of example, the viewed object may be a human organ or other surgical site. Also by way of example but not limitation, the curves A, B, C, D and E may represent object distances of 50, 75, 100, 125 and 150 mm. respectively. Curves A–E are merely for illustration and are not intended to constitute representations of actual data stored in E-proms 142. However, specific data constituting the relative positions of the CCD imaging unit ("Focus") and the zoom lens unit ("Zoom") required to achieve correct image focussing on the CCD imaging unit for different object distances are stored in E-prom 142 and are accessed by the computer during execution of the program illustrated in FIGS. 17–20. The data constituting the focus/zoom lookup table stored in E-prom 142 are pre-calculated according to the specific parameters of the lenses embodied in objective lens unit 48 and zoom unit 60, with such pre-calculation involving ray tracing and computer computation. No attempt is made herein to present specific data stored in the E-prom lookup table, since such data will vary with lens parameters and also since the procedure for deriving that data is well-known to persons skilled in the art.

FIGS. 16–19 are flow charts illustrating the software program for computer 138. Some or all of the software program and the lookup table may be permanently installed via firmware, or may be loaded into the computer from an external storage medium at the time of use. In either case, the program is designed so that after power has been applied to the system, the operator can cause the computer to automatically execute an initializing "reset" routine that results in motors 80 and 106 shifting imaging device 50 and zoom unit 60 to predetermined positions intermediate their mechanical limits, those predetermined positions being such that the image of a viewed object will be in focus on the image-receiving surface of the CCD imaging device when the front end of the endoscope is positioned to provide an object distance value of "n" mm, "n" being an arbitrary value selected for the initializing routine.

Figure 17:
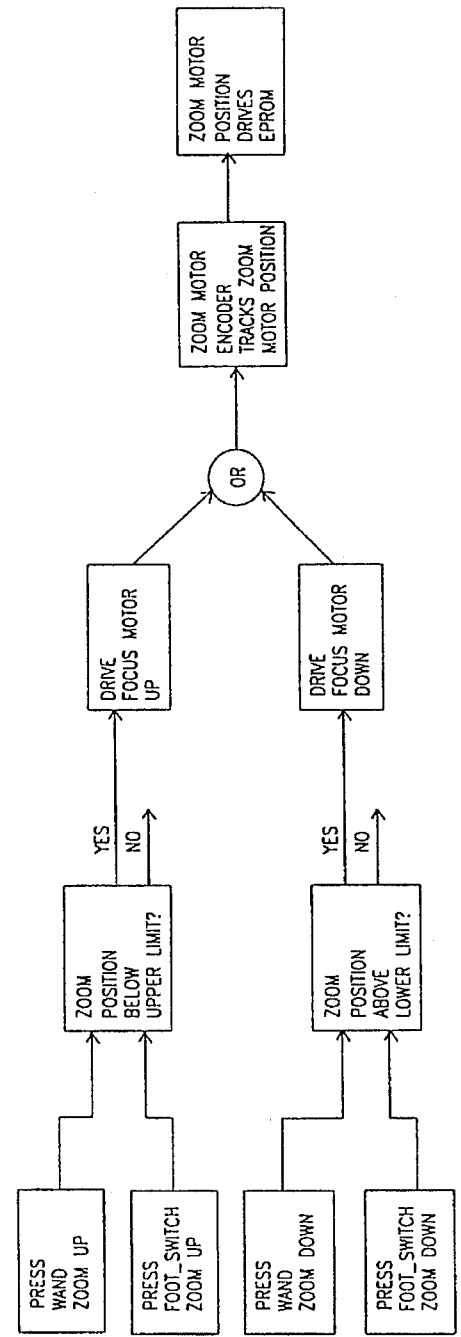
Figure 18:
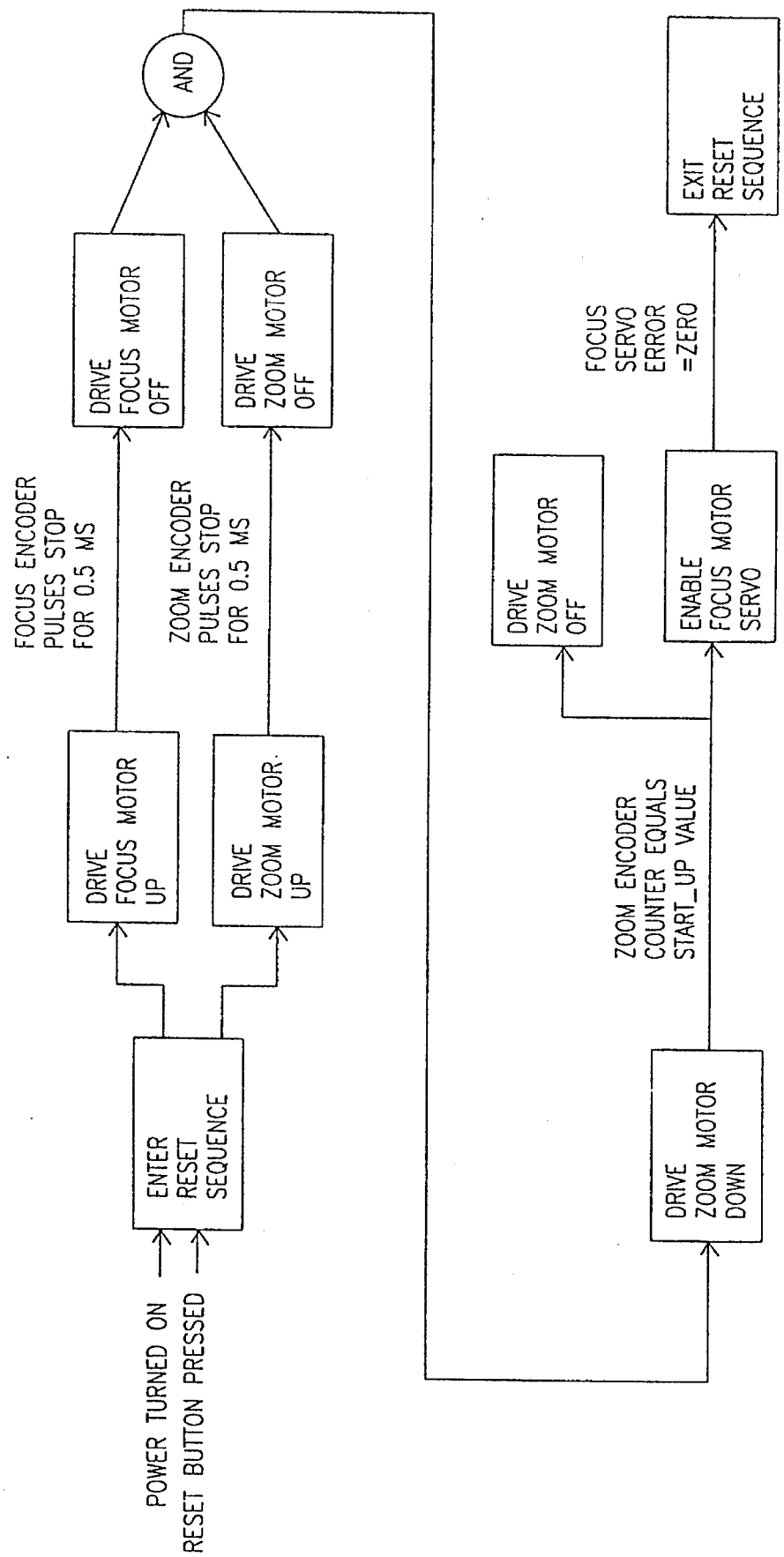
Figure 19:
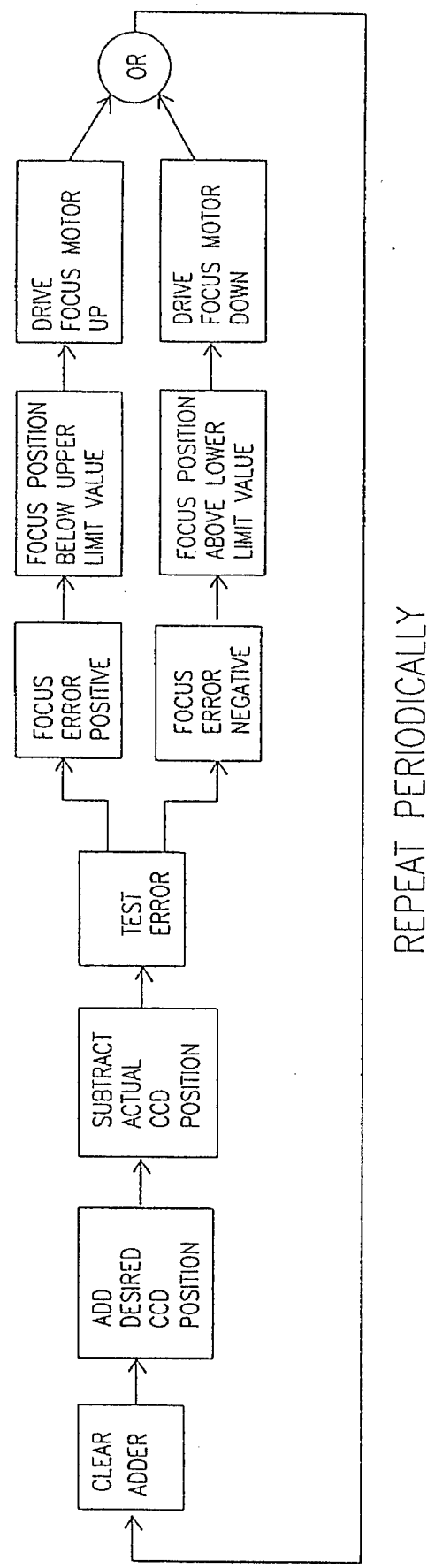

Operation of the endoscope is described hereinafter with reference to FIGS. 13–19. The control console is provided with a button-type reset switch (not shown) that is depressed by the physician or other user after the power has been turned on, thereby causing the computer to execute the aforementioned reset routine which is illustrated in FIGS. 18 and 19. That reset routine first involves operation of motors 80 and 106 so as to drive imaging device 50 and zoom unit 60 in an "UP" (forward) direction until their forward mechanical limits are reached, whereupon the mechanical load on the output shafts of the motors causes those shafts, and hence the corresponding encoders 122 and 124, to stop. Stopping of encoders 122 and 124 causes computer 138 to turn off motors 80 and 106 if no pulses have been generated by both encoders for 0.5 milliseconds ("ms").

As soon as both motors have been turned off, the computer (1) resets counters 162 and 164 to zero, (2) sets object distance counter 160 to a predetermined count "n" representing the desired initial object distance, and (3) actuates zoom motor 106 and causes it to move the zoom lens unit "Down" (rearwardly) to a predetermined start-up or reset position intermediate its distal and proximal mechanical limit positions. That start-up position is determined when the count in counter 164 equals a predetermined "start-up value" (see FIG. 18) accessed by the computer as part of the reset routine. Then motor 106 is turned off and the computer actuates focus motor 80 and causes it to move imaging device 50 in a "Down" (rearward) direction to a predetermined start-up position, the arrival at that start-up position being determined when the count in focus (CCD) position counter 162 as presented to comparator 174 matches a predetermined start-up value accessed from the E-prom 142 by the computer as part of the reset routine. At this point, the counts in counter 162 and 164 are start-up counts, whereby at any given time the control system can determine new changed positions of imaging device 50 and zoom lens unit 60 by determining how much the current counts in those counters differ from the start-up counts.

At this point, a focus motor servo control loop (FIG. 19) is activated, which control loop provides the following operation. As the imaging device 50 is moved in a "Down" direction to its predetermined start-up position, encoder 120 will generate pulses that are accumulated in counter 162. The output of object distance counter 160, preset by the computer to the predetermined start-up value "n" and the output of zoom motor position counter 164, are applied to E-prom 142 to obtain an output from the zoom/focus lookup table that has a value representing the desired imaging device position. The output from E-prom 142 (representing the desired CCD position) and the output of CCD position counter 162 (representing the actual CCD position) are applied to comparator 174. Depending on whether the actual CCD position represented by the output of counter 162 is "Up" or "Down" relative to the desired CCD position represented by the output of E-prom 142, the error signal produced by comparator 174 will be positive (+) or negative (−). If it is positive, and if the actual CCD position is below a predetermined upper limit value (the latter value is stored in the computer memory), focus motor 80 will be caused to move the imaging device in an "Up" direction. If the error signal is negative and the actual imaging device position is above a predetermined lower limit value stored in the computer memory, the focus motor will be caused to move the imaging device in a "Down" direction. In either case, the count of focus position counter output 162 will change and consequently the error signal from comparator 174 will change in value toward zero. At zero error signal value, the zoom motor will stop. Although not necessary, it is preferred for reasons of stability and accuracy, to program the focus servo control loop to periodically make a comparison in comparator 174, preferably every 20 microseconds as indicated in FIG. 19. This involves clearing the comparator (adder) at the start of each new comparison operation, as noted in FIG. 19.

At this point, if the distance between the endoscope and the viewed object ("object distance") is at the value for which the imaging device and the zoom unit are preset as a result of the reset routine, the image that is displayed by display device 140 will be in focus. Subsequently, if the object distance changes, e.g., as a result of the endoscope being moved, or the surgeon's point of interest is changed, the displayed image may go out of focus. In such event, the surgeon can reacquire a sharp focus by operating one or the other of buttons 8A and 8B. The resulting operation will cause counter 160 to be either increased or decreased by clocked pulses while switch 8A or 8B respectively is depressed. This changed value in counter 160 is applied to the zoom/focus lookup table, resulting in a new output value being transferred from the lookup table to comparator 174. The result is a change in the error signal output from comparator 174, which in turn is utilized by the servo control system to further operate motor 80 until the adjusted CCD position as measured by counter 162 again results in a zero error signal.

Once sharp focussing has been achieved, the image will remain in focus on the image-receiving surface of the CCD imaging device even though the operator utilizes buttons 8C or 8D to operate the zoom motor so as to zoom up or down with regard to the object being viewed. As seen in FIG. 17, the zoom motor encoder 122 tracks zoom motor position, and the output of the zoom motor encoder is used to drive the E-prom to a new output value. The new value obtained from E-prom 142 is compared with the signal output of counter 162 to modify the error signal. That error signal is then utilized in the servo-control loop to cause the focus motor to operate in a direction and for a duration sufficient to locate the CCD imaging device at a position which assures that sharp focussing of the image is achieved despite the change in field of view caused by zooming up or down.

The invention offers the advantage that when its main power switch (not shown) is turned on and/or the reset switch is actuated, its control system will automatically set the imaging device 50 and the zoom lens unit to a preselected position which provides a predetermined field of view with sharp focussing at the CCD device of the image seen by the objective lens. Thereafter, the operator has the advantage that by depressing either of the buttons 8C and 8D, the field of view may be changed without changing the object distance between the objective lens and the object being viewed. Additionally, if the need arises to change the position of the endoscope so as to change the object distance, the operator has the option of utilizing buttons 8A and 8B to refocus the image, and also the option of utilizing buttons 8C and 8D to change the field of view without again having to utilize the buttons 8A and 8B to change the position of the imaging device in a direction to restore or maintain a sharp image for viewing on displaying device 140.

The invention also offers the advantage that it is susceptible of various modifications. Thus different forms of imaging devices may be used. For example, the imaging component of the invention may utilize a BBD semiconductor imaging device rather than a CCD solid state element, as suggested by U.S. Pat. No. 4,488,039. Similarly, the number of lenses in the objective lens unit and also in the zoom lens unit may be changed without affecting operation of the invention. A further advantage resides in the fact that the provision of foot-operated switches in addition to the manually operated switches 144A–D is easily accomplished. Another advantage of the invention is that it utilizes conventional components. Still another advantage is that it provides reliable and direct-acting drive means for the imaging device and the zoom lens unit, and such drive means are so designed as to minimize the overall size of handle 2. Other possible modifications and advantages of the invention will be obvious to persons skilled in the art.

What is claimed is:

1. An endoscope apparatus comprising:

a handle assembly;

a tube having a distal end and a proximal end, with said proximal end anchored to said handle assembly;

an objective lens unit mounted in the distal end of said tube;

a shaft having a distal end and a proximal end, said shaft being disposed within and movable along the axis of said tube;

a solid state imaging device disposed within said tube and attached to said distal end of said shaft so as to be movable therewith along the axis of said tube, said imaging device having an image-receiving surface;

a zoom lens unit disposed within said tube between said objective lens unit and said imaging device, said zoom lens unit being moveable along the axis of said tube relative to said objective lens unit so as to cause the field of view of the image passed by said objective lens unit to be changed in accordance with the axial position of said zoom lens unit in relation to said objective lens unit;

first and second bidirectional electric motors carried by said handle assembly, each of said motors having an output shaft;

a first motion-transmitting means carried by said handle assembly and coupling said first motor to said shaft, whereby operation of said first motor will cause axial movement of said imaging device relative to said objective lens unit;

a second motion-transmitting means carried by said handle assembly and coupling said second motor to said zoom lens unit whereby operation of said second motor will cause axial movement of said zoom lens unit relative to said objective lens unit;

first and second user-operable switch means for selectively operating said first and second motors respectively; and control means responsive to operation of said second motor for operating said first motor according to a predetermined zoom/focus function so that each time said zoom unit changes position said imaging device will be positioned so that its image-receiving surface is in the focal plane of said zoom lens unit.

2. Apparatus according to claim 1 wherein said handle assembly comprises a housing and said first and second motors are mounted within said housing.

3. Apparatus according to claim 2 wherein said first and second motion-transmitting means comprise first and second gear systems respectively.

4. Apparatus according to claim 1 further including a second tube surrounding said tube, said second tube having a distal end and a proximal end and being sized and disposed so as to provide a space between it and said tube, and light-transmitting fibers disposed in said space for transmitting light to illuminate an object viewed by said objective lens unit, said light-transmitting fibers each having a distal end and a proximal end with the distal ends of said fibers terminating adjacent the distal ends of said tubes.

5. Apparatus according to claim 1 wherein said first user-operable switch means comprises first and second independently-operable switches, one for selectively operating said first motor in a forward direction and the other for selectively operating said first motor in a reverse direction, and said second user-operable switch means comprises second and third independently-operable switches, one for selectively operating said second motor in a forward direction and the other for selectively operating said second motor in a reverse direction.

6. Apparatus according to claim 1 wherein said handle assembly includes a housing for said first and second motors, and said first motion-transmitting means comprises a first gear system coupled to said shaft, said gear system being disposed within said housing.

7. Apparatus according to claim 6 wherein said second motion-transmitting means comprises a second gear system disposed within said housing and means coupling said gear system to said zoom lens unit.

8. Apparatus according to claim 6 wherein said first gear system comprises an elongate gear rack coupled by said shaft to said imaging device and a rotatable gear member driven by said first motor and engaged with said gear rack, whereby rotation of said gear member will cause said gear rack and said shaft to move axially relative to said tube.

9. Apparatus according to claim 1 wherein said second motion-transmitting means comprises at least one elongate gear rack attached to and movable with said zoom lens unit and rotatable gear means driven by said second motor and engaged with said at least one gear rack, whereby rotation of said gear means will cause said at least one gear rack and said zoom lens unit to move axially relative to said tube.

10. Apparatus according to claim 1 wherein said first motion-transmitting means comprises an elongate first gear rack coupled to said shaft and extending lengthwise of said, and a first gear member driven by said first motor and engaged with said first gear rack, whereby rotation of said first gear member will cause said gear rack and said imaging device to move axially relative to said tube, and said second motion-transmitting means comprises first and second rods connected to said zoom lens unit, and gear means coupling said second motor and said first and second rods, whereby rotation of said second gear member will cause said second and third rods and said zoom lens unit to move axially relative to said tube.

11. Apparatus according to claim 10 having a bushing fixed within said tube, with said shaft extending within and movable axially relative to said bushing between said handle assembly and said imaging device.

12. Apparatus according to claim 11 wherein said bushing has first and second longitudinally-extending grooves, and said first and second rods are disposed within and extend lengthwise of said first and second grooves within said tube.

13. Apparatus according to claim 1 further comprising first and second means for sensing the extent and direction of movement of said zoom lens unit and said imaging device relative to said objective lens unit and for producing first and second output signals indicative of the extent and direction of said movement of said zoom lens unit and said imaging device, and means for coupling said first and second output signals to said control means for use in controlling the relative positions of said zoom lens unit and said imaging device so as to position said imaging device at the focal plane of said zoom lens unit, whereby the image seen by said objective lens and projected by said zoom lens unit is in focus at the image-receiving surface of said imaging device.

14. Apparatus according to claim 1 further comprising first and second sensing means for sensing the extent and direction of movement of said zoom lens unit and said imaging device respectively relative to said objective lens unit and for producing first and second output signals respectively indicative of the extent and direction of movement of said zoom lens unit and said imaging device respectively, and means for coupling said output signals of said first and second sensing means to said control means for use in controlling the relative positions of said zoom lens unit and said imaging device so that at each position of said zoom lens unit said imaging device is positioned at the focal plane of said zoom lens unit, whereby the image seen by said objective lens and projected by said zoom lens unit is in focus at the image-receiving surface of said imaging device.

15. Apparatus according to claim 14 wherein said first and second sensing means comprise first and second encoders coupled to said first and second electric motors respectively.

16. An endoscope apparatus according to claim 14 wherein said control means comprises an electronic lookup table containing data identifying the relative positions of said zoom lens unit and said imaging device that are required in order to maintain the image of any object seen by said objective lens unit in focus on the image receiving surface of said imaging device at various settings of said zoom lens unit for a given object distance, electronic means responsive to said output signals for accessing the data in said lookup table and for generating motor control signals in accordance with the accessed data, and means for applying said motor control signals to said first and second motors.

17. An endoscope apparatus comprising:

a handle assembly comprising a housing;

an inner tube having a distal end and a proximal end, with said proximal end anchored to said handle assembly and extending away from said housing;

an outer tube surrounding said inner tube, said outer tube having a distal end and a proximal end, with said proximal end anchored to said handle assembly and extending away from said housing;

a solid state imaging device mounted within and movable along said inner tube;

an objective lens unit mounted within and fixed to the distal end of said inner tube;

a zoom lens unit mounted within and movable along said inner tube, said zoom lens unit being disposed between said objective lens unit and said imaging device;

a plurality of light-transmitting fibers disposed between said inner and outer tubes, said fibers extending substantially to the distal end of said inner tube so that light transmitted thereby will illuminate the objective field;

first bi-directional electromechanical means for moving said zoom lens unit along said inner tube toward or away from said objective lens unit, said first electromechanical means comprising a first reversible electrical motor having an output shaft enclosed by said housing and first gear means coupling said output shaft to said zoom lens unit, whereby energization of said first motor will cause movement of said zoom lens unit along said inner tube according to the mode of energization of said motor;

second bidirectional electromechanical means for moving said imaging device along said inner tube toward or away from said objective lens unit and said zoom lens unit, said second electromechanical means comprising a second reversible electrical motor having an output shaft enclosed by said housing and second gear means coupling the output shaft of said second electrical motor to said imaging device, whereby energization of said second motor will cause movement of said imaging device along said inner tube according to the mode of energization of said second motor;

first and second sensing means coupled to said first and second motors respectively for providing first and second output signals indicative of the extent and direction of movement of said zoom lens unit and said imaging device respectively by operation of said motors, and means responsive to said first and second output signals for determining the position of said zoom lens unit and said imaging device relative to predetermined startup reference positions.

18. Apparatus according to claim 17 wherein said first gear means includes a gear rack that is enclosed by said housing and is coupled to said zoom lens unit.

19. Apparatus according to claim 18 wherein said second gear means includes a gear rack that is enclosed by said housing and is coupled to said imaging device.

20. Apparatus according to claim 17 further comprising a servo control system for operating said second motor in response to operation of said first motor according to a predetermined zoom/focus function, whereby to automatically position said imaging device at the focal plane of said zoom lens unit so as to maintain the image seen by said objective lens unit in sharp focus at said imaging device.

21. Apparatus according to claim 20 wherein said handle assembly includes first, second, third and fourth manually operable switches having actuating members accessible to the endoscope user, means connecting said first and second switches to said first motor, whereby when said first switch is operated, said first motor is energized so as to cause said imaging device to move toward said distal end of said inner tube and when said second switch is operated said first motor is energized so as to cause said imaging device to move away from said distal end of said inner tube; and means connecting said third and fourth switches to said second motor, whereby when said third switch is operated said second motor is energized so as to cause said zoom lens unit to move toward said distal end of said inner tube and when said fourth switch is operated said second motor is energized so as to cause said zoom lens unit to move away from said distal end of said inner tube.

22. An endoscope apparatus according to claim 17 wherein said handle assembly comprises first, second, third and fourth switch means, means connecting said first and second switch means to said first motor so that when said first switch means is operated said first motor is energized so as to cause said imaging device to move forward toward said objective lens and when said second switch means is operated said first motor is a energized so as to cause said imaging device to move rearwardly away from said objective lens unit; and means connecting said third and fourth switch means to said second motor so that when said third switch means is operated said second motor is energized so as to cause said zoom lens unit to move forward toward said objective lens unit and when said fourth switch means is operated said second motor is energized so as to cause said zoom lens unit to move rearwardly away from said objective lens unit.

23. An endoscope apparatus comprising:

a handle assembly comprising a housing and at least first and second button-actuated switch means;

an inner tube having a distal end and a proximal end, with said proximal end fixed to said handle assembly and extending away from said housing;

an outer tube surrounding said inner tube, said outer tube having a distal end and a proximal end, with said proximal end fixed to said handle assembly and extending away from said housing;

a solid state imaging device mounted within and movable along said inner tube;

an objective lens unit mounted within and fixed to said inner tube at the distal end thereof;

a zoom lens unit mounted within and movable along said inner tube, said zoom lens unit being disposed between said objective lens unit and said imaging device;

a plurality of light-transmitting fibers disposed between said inner and outer tubes, said fibers extending substantially to the distal end of said inner tube so that light transmitted thereby will illuminate the objective field;

first bi-directional electromechanical means for moving said zoom lens unit along said inner tube toward or away from said objective lens unit, said first electromechanical means comprising (a) a first reversible electrical motor having an output shaft, said first motor being mounted to said handle assembly and being enclosed by said housing, and (b) first motion-transmitting means coupling said output shaft to said zoom lens unit, means connecting said first switch means in selectively operable relation with said first reversible electrical motor, whereby actuating said first switch means energizes said first motor and thereby causes movement of said zoom lens unit along said inner tube according to the mode of energization of said first motor; and second bi-directional electromechanical means for moving said imaging device along said inner tube toward or away from said objective lens unit and said zoom lens unit, said second electromechanical means comprising (a) a second reversible electrical motor having an output shaft, said second motor being mounted to said handle assembly and being enclosed by said housing, and (b) second motion transmitting means coupling the output shaft of said second electrical motor to said imaging device, means connecting said second switch means in selectively operable relation with said second reversible electrical motor, whereby actuating said second switch means energizes said second motor and thereby causes movement of said imaging device along said inner tube according to the mode of energization for said second motor.

24. An endoscope comprising:

a handle assembly comprising a handle and first, second, third, and fourth manually-operable switch means carried by said handle, each of said switches having an actuating button on said handle;

an inner tube having a distal end and a proximal end with said proximal end anchored to said handle assembly;

an outer tube surrounding said inner tube and anchored to said handle assembly;

a solid state imaging device mounted within and movable along said inner tube;

an objective lens unit mounted within and fixed to the distal end of said inner tube;

a zoom lens unit mounted within and movable along said inner tube; said zoom lens unit being disposed between said objective lens unit and said imaging device;

a plurality of light-transmitting fibers disposed between said inner and outer tubes, said fibers extending substantially to the distal end of said inner tube so that light transmitted thereby will illuminate the objective field;

first bi-directional electromechanical means for moving said zoom lens unit along said inner tube toward or away from said objective lens unit, said first electromechanical means comprising a first reversible electrical motor having an output shaft and first gear means coupling said output shaft to said zoom lens unit;

means coupling said first and second switch means in operable relation with said first reversible electrical motor, whereby depressing the actuating button of said first switch means energizes said first motor so as to cause forward movement of said zoom lens unit along said inner tube and depressing the actuating button of said second switch means energizes said first motor so as to cause rearward movement of said zoom lens unit along said inner tube;

second bi-directional electromechanical means for moving said imaging device along said inner tube toward or away from said objective lens unit and said zoom lens unit, said second electromechanical means comprising a second reversible electrical motor having an output shaft and second gear means coupling the output shaft of said second electrical motor to said imaging device;

means coupling said third and fourth switch means in operable relation with said second reversible electrical motor, whereby depressing the actuating button of said third switch button energizes said second motor so as to cause forward movement of said imaging device along said inner tube and depressing the actuating button of said fourth switch button energizes said second motor so as to cause rearward movement of said imaging device along said inner tube, and:

first and second sensing means for sensing the extent and direction of movement of said zoom lens unit and said imaging device respectively relative to said objective lens unit and for producing first and second output signals respectively indicative of the extent and direction of movement of said zoom lens unit and said imaging device respectively, and means for coupling said output signals of said first and second sensing means to said control means for use in controlling the relative positions of said zoom lens unit and said imaging device so that at each position of said zoom lens unit said imaging device is positioned at the focal plane of said zoom lens unit, whereby the image seen by said objective lens and projected by said zoom lens unit is in focus at the image-receiving surface of said imaging device.

25. An endoscope apparatus comprising:

a handle assembly comprising a housing;

an outer tube having a distal end and a proximal end, with said proximal end anchored to said handle assembly;

an inner tube having a distal end and a proximal end, said inner tube being mounted within said outer tube and having its proximal end anchored to said handle assembly;

an objective lens unit mounted in the distal end of said inner tube;

a shaft having a distal end and a proximal end, said shaft being disposed within and movable along the axis of said inner tube;

a solid state imaging device disposed within said inner tube and attached to said distal end of said shaft so as to be movable therewith along the axis of said inner tube;

a zoom lens unit disposed within said inner tube between said objective lens unit and said imaging device, said zoom lens unit being moveable along the axis of said inner tube relative to said objective lens unit so as to cause the magnification of the image passed by said objective lens unit to be changed in accordance with the axial position of said zoom lens unit in relation to said objective lens unit;

first and second drive means carried by said handle assembly, said first and second drive means comprising first and second reversible electric motors respectively mounted within said housing;

a first motion-transmitting means coupling said first electric motor to said shaft, whereby operation of said first electric motor will cause axial movement of said imaging device relative to said objective lens unit;

a second motion-transmitting means coupling said second drive means to said zoom lens unit whereby operation of said second electric motor will cause axial movement of said zoom lens unit relative to said objective lens unit and said zoom lens unit;

light-transmitting means disposed between said first and second tubes for transmitting light to illuminate an object viewed by said objective lens unit;

means attached to said handle assembly for connecting said proximal end of said light transmitting means to a light source;

first switch means for coupling power to said first electric motor, said first switch means being selectively operable to (a) energize said first motor so that said first motor will operate in a first direction whereby to drive said imaging device toward said objective lens unit or (b) energize said first motor so that said first motor will operate in a second direction opposite to said first direction whereby to drive said imaging device away from said objective lens unit;

second switch means for coupling power to said second electric motor, said first switch means being selectively operable to (a) energize said second motor so that said second motor will operate in a first direction whereby to drive said zoom lens unit toward said objective lens unit or (b) energize said second motor so that said second motor will operate in a second direction opposite to said first direction whereby to drive said zoom lens unit away from said objective lens unit, and control means responsive to operation of said second motor for operating said first motor so that a change in the position of said zoom lens unit will cause said imaging device to move so as to maintain the image seen by the objective lens unit in sharp focus at said imaging device.

26. An endoscope apparatus according to claim 25 wherein said first and second switch means have user-accessible actuating members on the outside of said housing.

27. An endoscope apparatus according to claim 26 further including first and second encoders coupled to and driven by said first and second electric motors respectively, said first and second encoders providing first and second output signals representative of the direction and extent of movement of said imaging device and said zoom lens unit in response to operation of said first and second electric motors respectively, said control means being responsive to said first and second encoder output signals in respect of said first motor so as to maintain the image seen by said objective lens unit in sharp focus at said imaging device.

28. An endoscope apparatus according to claim 27 wherein said control means further includes an electronic look-up table comprising data identifying the relative positions of said zoom lens unit and said imaging device that are required in order to maintain the image of any object seen by said objective lens unit in focus on the image receiving surface of said imaging device at various settings of said zoom lens unit for a given object distance, and said control means further includes electronic means responsive to said encoder output signals for accessing the data in said lookup table and for generating motor control signals in accordance with the accessed data, and means for applying said motor control signals to said first and second motors.

29. An endoscope apparatus according to claim 27 wherein said lookup table comprises data representing a plurality of curves each constituting a plot of different positions of (1) the zoom lens unit in relation to the objective lens unit versus (2) the corresponding distances between the imaging device and the objective lens unit that is required to assure that the image-receiving surface of the imaging device is in the focal plane of the zoom lens unit.

30. An endoscope apparatus according to claim 27 wherein said control means comprises a focus switch input circuit controlled by said first switch means for providing output pulses in accordance with operation of said first motor, a first object distance counter responsive to the output signal from said focus switch input circuit for providing an output signal representative of the distance from the objective lens to the viewed object, a second focus position counter responsive to the output signal from said first encoder for providing an output signal representative of the position of said imaging device, and a third zoom position counter responsive to the output signal from said second encoder for providing an output signal representative of the position of said zoom lens unit.

31. An endoscope apparatus comprising:

a handle assembly comprising a housing;

an outer tube having a distal end and a proximal end, with said proximal end anchored to said handle assembly;

an inner tube having a distal end and a proximal end, said inner tube being mounted within said outer tube and having its proximal end anchored to said handle assembly;

an objective lens unit mounted in the distal end of said inner tube;

light-transmitting means disposed between said outer and inner tubes for transmitting light to illuminate an object viewed by said objective lens circuit;

a shaft having a distal end and a proximal end, said shaft being disposed within and movable along the axis of said inner tube;

a solid state imaging device disposed within said inner tube and attached to said distal end of said shaft so as to be movable therewith along the axis of said inner tube;

a zoom lens unit disposed within said inner tube between said objective lens unit and said imaging device, said zoom lens unit being moveable along the axis of said inner tube relative to said objective lens unit so as to cause the magnification of the image passed by said objective lens unit to be changed in accordance with the axial position of said zoom lens unit in relation to said objective lens unit;

first and second drive means carried by said handle assembly, said first and second drive means comprising first and second reversible electric motors respectively mounted within said housing;

a first motion-transmitting means coupling said first electric motor to said shaft, whereby operation of said first electric motor will cause axial movement of said imaging device relative to said objective lens unit;

a second motion-transmitting means coupling said second drive means to said zoom lens unit whereby operation of said second electric motor will cause axial movement of said zoom lens unit relative to said objective lens unit and said zoom lens unit;

first switch means for coupling power to said first electric motor, said first switch means being selectively operable to (a) energize said first motor so that said first motor will operate in a first direction whereby to drive said imaging device toward said objective lens unit or (b) energize said first motor so that said first motor will operate in a second direction opposite to said first direction whereby to drive said imaging device away from said objective lens unit;

second switch means for coupling power to said second electric motor, said first switch means being selectively operable to (a) energize said second motor so that said second motor will operate in a first direction whereby to drive said zoom lens unit toward said objective lens unit or (b) energize said second motor so that said second motor will operate in a second direction opposite to said first direction whereby to drive said zoom lens unit away from said objective lens unit, and first and second encoder means responsive to operation of said first and second motors for generating first and second signal pulses representative of the direction and extent of movement of said imaging device and said zoom lens unit in response to operation of said first and second motors respectively; and a servo control circuit for operating said first motor in response to operation of said second motor in accordance with a predetermined zoom/focus function, so that a change in position of said zoom lens unit caused by operation of said second motor results in a change in position of said imaging device sufficient to focus the viewed image on the image plane of said imaging device.

32. An endoscope according to claim 31 wherein said control means comprises:

a focus position counter coupled to respond to said first signal pulses and provide an output signal representative of the number of said first signal pulses it receives;

a zoom position counter coupled to respond to said second signal pulses and provide an output signal representative of the number of said second signal pulses it receives;

a focus switch input circuit for generating third signal pulses in response to operation of said second motor by operation of said second switch means;

an object distance counter coupled to respond to said third signal pulses and provide an output signal representative of the number of third pulses it receives;

computer means including an electronic look-up table for generating a focus motor drive signal having a value derived from said look-up table that varies as a function of the output signals of said first, second and third counters, and means for applying said focus motor drive signal to said first motor whereby to adjust the position of said imaging device.

33. An endoscope according to 32 further including a zoom switch input circuit for generating fourth pulses in response to operation of said second switch means, means responsive to said fourth pulses for generating a zoom motor drive signal in response to said fourth pulses; and means for applying said zoom motor drive signals to said second motor so as to cause adjustment of the position of said zoom lens unit.

* * * * *

UNITED STATES PATENT AND TRADEMARK OFFICE
CERTIFICATE OF CORRECTION

PATENT NO.    : 5,582,576
DATED         : December 10, 1996
INVENTOR(S)   : Koichiro Hori et al It is certified that error appears in the above-indentified patent and that said Letters Patent is hereby corrected as shown below:

Claim 10, column 13, line 18, the word "tube" should be inserted after the word "said";

Claim 22, column 15, line 35, the word "a" should be deleted before the word "energized"; and Claim 23, column 16, line 29, the word "for" should be changed to -- of --.

Signed and Sealed this

Eighteenth Day of March, 1997

Attest:

BRUCE LEHMAN

*Attesting Officer*   Commissioner of Patents and Trademarks